US012760120B2

(12) United States Patent
Rosenkranz et al.

(10) Patent No.: US 12,760,120 B2
(45) Date of Patent: Oct. 13, 2026

(54) VISCOSITY REDUCING EXCIPIENTS AND COMBINATIONS THEREOF FOR HIGHLY CONCENTRATED PROTEIN FORMULATIONS

(71) Applicant: Merck Patent GmbH, Darmstadt (DE)

(72) Inventors: Tobias Rosenkranz, Darmstadt (DE); Stefan Braun, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 664 days.

(21) Appl. No.: 18/015,378

(22) PCT Filed: Jul. 12, 2021

(86) PCT No.: PCT/EP2021/069374

§ 371 (c)(1),
(2) Date: Jan. 10, 2023

(87) PCT Pub. No.: WO2022/013171

PCT Pub. Date: Jan. 20, 2022

(65) Prior Publication Data

US 2023/0279146 A1 Sep. 7, 2023

(30) Foreign Application Priority Data

Jul. 13, 2020 (EP) .................................... 20185558
Oct. 28, 2020 (EP) .................................... 20204464

(51) Int. Cl.

| | |
|---|---|
| ***C07K 16/40*** | (2006.01) |
| ***A61K 47/18*** | (2017.01) |
| ***A61K 47/20*** | (2006.01) |
| ***A61K 47/22*** | (2006.01) |
| ***A61K 47/24*** | (2006.01) |
| ***C07K 16/24*** | (2006.01) |

(52) U.S. Cl.

CPC ............ *C07K 16/40* (2013.01); *A61K 47/183* (2013.01); *A61K 47/20* (2013.01); *A61K 47/22* (2013.01); *A61K 47/24* (2013.01); *C07K 16/241* (2013.01)

(58) Field of Classification Search

None
See application file for complete search history.

(56) References Cited

U.S. PATENT DOCUMENTS

| | | | | |
|---|---|---|---|---|
| 1,712,999 | A | 5/1929 | Kreisinger et al. | |
| 7,172,999 | B2 | 2/2007 | Mattern et al. | |
| 10,166,293 | B2 | 1/2019 | Liu et al. | |
| 10,646,569 | B2 | 5/2020 | Shenoy | |
| 11,459,401 | B2 | 10/2022 | Teran et al. | |
| 2013/0058958 | A1 | 3/2013 | Bowen et al. | |
| 2014/0023655 | A1 | 1/2014 | Monck et al. | |
| 2018/0333493 | A1 * | 11/2018 | Shenoy | C07K 16/06 |
| 2020/0352857 | A1 | 11/2020 | Gu et al. | |
| 2021/0162046 | A1 | 6/2021 | Soane et al. | |
| 2022/0088200 | A1 | 3/2022 | Zillmann et al. | |

FOREIGN PATENT DOCUMENTS

| | | | | |
|---|---|---|---|---|
| DE | 202016005938 | U | 12/2016 | |
| JP | 2014516924 | A | 7/2014 | |
| JP | 2015017042 | A | 1/2015 | |
| JP | 2016534141 | A | 11/2016 | |
| JP | 2020510079 | A | 4/2020 | |
| WO | 02/30463 | A2 | 4/2002 | |
| WO | 2011139718 | A1 | 11/2011 | |
| WO | 2015/196187 | A1 | 12/2015 | |
| WO | 2015196091 | A1 | 12/2015 | |
| WO | WO-2016109822 | A1 * | 7/2016 | A61K 47/183 |
| WO | 2017070501 | A1 | 4/2017 | |
| WO | 2018067987 | A1 | 4/2018 | |
| WO | 2018200533 | A1 | 11/2018 | |
| WO | 2018211517 | A1 | 11/2018 | |
| WO | WO-2018204374 | A1 * | 11/2018 | A61P 35/00 |
| WO | 2019201904 | A1 | 10/2019 | |

OTHER PUBLICATIONS

Silva, F. C. (2018). Fouling of Nanofiltration Membranes. InTech. doi: 10.5772/intechopen.75353 (Year: 2018).*
International Search report PCT/EP2021/069374 dated Sep. 21, 2021 (pp. 1-5).
Connolly et al: Weak Interactions Govern the Viscosity of Concentrated Antibody Solutions: High-Throughput Analysis Using the Diffusion Interaction Parameter, Biophysical Journal, 103(1),2012, pp. 69-78.
Guo et al: "Structure-Activity Relationship for Hydrophobic Salts as Viscosity-Lowering Excipients for Concentrated Solutions of Monoclonal Antibodies", Pharm. Research, 2012, 29(11), pp. 3102-3109.
Tiškov T.M. et al. Sovremennye vspomogatel'nye vesestva [Modern Excipients], Modern Problems of Science and Education, 2015, No. 2-1 (par. 1).
Tallarida Ronald J., "Quantitative Methods for Assessing Drug Synergism", Genes & Cancer, Nov. 2011, vol. 2, No. 11, pp. 1003-1008.

* cited by examiner

*Primary Examiner* — Robert A Wax
*Assistant Examiner* — Julia A Rossi
(74) *Attorney, Agent, or Firm* — Csaba Henter; MILLEN, WHITE, ZELANO & BRANIGAN, P.C.

(57) ABSTRACT

The present invention relates to liquid compositions and formulations comprising a protein having a reduced viscosity and/or increased stability. Furthermore, the invention relates to methods for reducing the viscosity and/or increasing the stability of a protein solution.

17 Claims, 16 Drawing Sheets

VISCOSITY REDUCING EXCIPIENTS AND COMBINATIONS THEREOF FOR HIGHLY CONCENTRATED PROTEIN FORMULATIONS

TECHNICAL FIELD

The present invention relates to liquid compositions and formulations comprising a protein having a reduced viscosity and/or increased stability. Furthermore, the invention relates to methods for reducing the viscosity and/or increasing the stability of a protein solution.

BACKGROUND

Since the FDA authorized the first biopharmaceutical in 1982, many other biologic drugs have followed suit. Most of these are monoclonal antibodies (mAB) or related formats such as bi-specific antibodies or antibody fragments. While these drugs offer unique opportunities in terms of efficacy, their structure and size pose various challenges.

Antibodies and other protein therapeutics are usually administered parenterally, for example by intravenous (iv), intramuscular (im) or subcutaneous (sc) route. Subcutaneous injection is particularly popular for the delivery of protein therapeutics due to its potential to simplify patient administration (fast, low-volume injection) and reduce treatment costs (shorter medical assistance). To ensure patient compliance, it is desirable that subcutaneous injection dosage forms be isotonic and can be injected in small volumes (<2.0 ml per injection site). To reduce the injection volume, proteins are often administered with a concentration of 1 mg/ml to 150 mg/ml.

At the same time, mAb-based therapies usually require several mg/kg dosing. The combination of high therapeutic dose and low injection volume thus leads to a need for highly concentrated formulations of therapeutic antibodies. However, being large proteins, antibodies possess a multitude of functional groups in addition to a complex three-dimensional structure. This makes their formulation difficult, particularly when a high concentration is required.

One of the main problems with high concentration protein solutions is viscosity. At high concentrations, proteins tend to form highly viscous solutions largely due to non-native self-association. Additionally, proteins show an increased rate of aggregation and particle formation at such high concentrations.

These problems concern both the manufacturing process and the administration to the patient. In the manufacturing process, highly concentrated protein formulations that are highly viscous present particular difficulties for ultrafiltration and sterile filtration. In addition, tangential flow filtration is often used for the buffer exchange and for the increase of protein concentration. However, because viscous solutions show an increased back pressure and shear stress during injection and filtration, the therapeutic protein is potentially destabilized and/or process times are prolonged. Said increased shear stress frequently results in a loss of product. Both aspects adversely affect process economics.

At the same time, high viscosity is unacceptable when it comes to administration as it significantly limits the injectability of the protein.

To solve these problems and/or to improve the stability of the solution, additives and excipients such as sucrose and sodium chloride are usually added in higher concentrations to biopharmaceutical formulations. However, the resulting solutions often cause pain due to high injection forces and resulting tissue damages. Some of these solutions may even be no longer administrable resulting in a lack of therapeutic options for the patient.

As an alternative, different excipients such as salts, camphor-10-sulfonic acid and specific amino acids, e.g. arginine, histidine, lysine and proline, have been explored as a way of reducing the viscosity of certain high-concentration protein therapeutics. Guo et al. suggest that salts having hydrophobic, bulky, and aliphatic ionic constituents may act as potent viscosity-lowering excipients (Guo Z. et al., *Pharmaceutical Research;* 2012, 29(11):3102-9). Furthermore, WO 02/30463, WO 15/196091, WO 15/196187, WO 17/070501 and WO 19/201904 disclose different viscosity reducing excipients.

However, formulating proteins like monoclonal antibodies requires a careful selection of formulation additives and/or excipients to avoid protein denaturation and loss of biological activity. In addition, the excipients need to be pharmaceutically safe and physiologically compatible so to avoid any undesired side effects such as allergic reactions.

Consequently, the pharmaceutical industry has a strong need for additional pharmaceutically acceptable, viscosity-reducing excipients, especially as an alternative when standard solutions based on NaCl and amino acids such as mentioned above fail.

The problem to be solved is therefore the provision of excipients that can effectively reduce the viscosity of a protein solution and/or increase stability thereof. Furthermore, the problem to be solved is the provision of excipient combinations that can effectively reduce the viscosity of a protein solution and/or increase stability thereof. Yet another problem to be solved is that many viscosity reducing excipients used at relevant concentrations can adversely affect protein stability.

During the bioprocess, the solutions have to be pumped through tubing and chromatography columns. At high viscosities, the flow rate through such columns is limited by said viscosity which leads to longer processing times, significant protein losses during chromatography or might lead to complete non-processability of the protein solution. Furthermore, when passing through a connector from the narrow tube into a less narrow column, shear forces may occur. Shear stress is a typical reason for proteins to denature and potentially to aggregate and thereby reducing the yield of the process. Obviously, such shear stress induced aggregation has an adverse effect on process economics. Moreover, the gel bed within the chromatography column may be damaged by the high pressure.

Additionally, some proteins are formulated into high concentration through tangential flow filtration (TFF). When the viscosity of the solution becomes critical, a gel-like layer may be formed near the membrane. Especially the membrane flux is significantly reduced yielding to an increased processing time and therefore to significant higher manufacturing costs. As discussed before, also during TFF shear stress may occur yielding to insoluble protein aggregates and a reduced yield.

Generally, it has been observed that highly viscous solutions develop a certain stickiness making it difficult to recover the complete solution from containers, out of tubing or to remove the entire substance from processing systems. This loss of substance leads to a significantly reduced product yield with the obvious adverse effect on process economics.

Furthermore, a problem to be solved is the provision of excipient combinations that can effectively reduce the viscosity of a protein solution.

Yet another problem to be solved is that many viscosity reducing excipients used at relevant concentrations can adversely affect protein stability. Hence a further problem to be solved is the provision of excipient combinations that can effectively reduce the viscosity of a protein solution and that show an improved protein stability compared to one viscosity reducing excipient alone used in a higher concentration that results in a similar viscosity reduction compared to the combination.

High viscosity of protein solutions causes numerous difficulties in bioprocessing. Since known additives which hitherto are used for reducing the viscosity in corresponding protein solutions do not lead to sufficient viscosity-reducing effects in many cases, it is an object of the present invention to find new possibilities whereby corresponding viscosity-lowering effects can be improved and adverse effects on process economics can be reduced.

An additional subject of the present invention is a method for reducing the viscosity of liquid protein compositions in bioprocess, comprising the step of combining the liquid protein composition with at least one first viscosity reducing excipient selected from the group consisting of cyanocobalamin, pyridoxine, ascorbic acid, folic acid or salts thereof, thiamine, thiamine monophosphate, thiamine pyrophosphate, guanidine hydrochloride, quinine hydrochloride and paracetamol.

SUMMARY OF THE INVENTION

The problem is solved by a liquid composition comprising a protein and at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. The problem is solved by a liquid composition comprising a protein and at least one first viscosity reducing excipient as described above and at least one second viscosity reducing excipient, preferably selected from the group consisting of valine, proline, leucine, isoleucine, phenylalanine, arginine, ornithine, carnitine, meglumine, camphorsulfonic acid and benzenesulfonic acid.

The use of at least two viscosity reducing excipients allows to overcome the problem that many viscosity reducing excipients used at relevant concentrations can adversely affect protein stability by allowing for the use of a lower amount of each individual excipient and leveraging the stabilizing effect of a second viscosity reducing excipients.

Likewise, the problem is solved by a method for reducing the viscosity of a protein solution, comprising a step of adding at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol to the protein solution. The problem is solved by a method for reducing the viscosity of a protein solution, comprising a step of adding at least one further second excipient selected from the group consisting of valine, proline, leucine, isoleucine, phenylalanine, arginine, ornithine, carnitine, meglumine, camphorsulfonic acid and benzenesulfonic acid.

The problem is also solved by a method for increasing the stability of a protein solution, comprising a step of adding at least one first excipient is selected from the group consisting of valine, leucine, ascorbic acid, cyanocobalamin and proline to the solution.

The problem is further solved by a composition comprising a protein and a viscosity-reducing solution comprising at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. The problem is solved by a composition comprising a protein and at least one further second excipient selected from the group consisting of valine, proline, leucine, isoleucine, phenylalanine, arginine, ornithine, carnitine, meglumine, camphorsulfonic acid and benzenesulfonic acid.

Furthermore, the problem is solved by a liquid formulation of a protein, especially a therapeutic protein, comprising at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. The problem is solved by a liquid formulation of a protein, especially a therapeutic protein, comprising at least one further second excipient selected from the group consisting of valine, proline, leucine, isoleucine, phenylalanine, arginine, ornithine, carnitine, meglumine, camphorsulfonic acid and benzenesulfonic acid.

Furthermore, the problem is solved by a lyophilized protein formulation of a composition comprising a protein and at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. The problem is solved by a lyophilized protein formulation of a composition comprising a protein and at least one further second excipient selected from the group consisting of valine, proline, leucine, isoleucine, phenylalanine, arginine, ornithine, carnitine, meglumine, camphorsulfonic acid and benzenesulfonic acid.

Furthermore, the problem is solved by a kit comprising a composition comprising a protein and at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. The problem is solved by a kit comprising a composition comprising a protein and at least one further second excipient selected from the group consisting of valine, proline, leucine, isoleucine, phenylalanine, arginine, ornithine, carnitine, meglumine, camphorsulfonic acid and benzenesulfonic acid.

An additional subject of the present invention is a method for reducing the viscosity of liquid protein compositions in a bioprocess, comprising the step of combining the liquid protein composition with at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. Preferably the liquid protein composition further comprises a second viscosity reducing excipient selected from the group consisting of valine, proline, leucine, isoleucine, phenylalanine, arginine, ornithine, carnitine, meglumine, camphorsulfonic acid and benzenesulfonic acid.

DETAILED DESCRIPTION OF THE INVENTION

The invention is directed to a pharmaceutical composition or liquid formulation comprising a protein and at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol.

A "protein" is herein defined as a polymer of amino acids linked to each other by peptide bonds to form a polypeptide. Proteins can be naturally occurring or non-naturally occurring, synthetic, or semisynthetic. The term "protein" is understood to also cover peptides, oligopeptides, polypeptides and any therapeutic protein as defined below. Preferably the "protein" has a length sufficient to form a detectable tertiary structure.

Without wanting to be bound by a mechanism, it is believed that the viscosity reducing effect of the compositions and formulations according to the invention is based upon an interaction between the excipients and the amino acid residues of the protein. Because all proteins are built from the same pool of amino acids, the effects described herein are thus applicable to all proteins. The compositions and formulations according to the invention therefore have an advantageous effect on any protein irrespective of its sequence, size and structure.

The invention is also directed to liquid formulations of therapeutic proteins comprising cyanocobalamin, pyridoxine, ascorbic acid, folic acid, thiamine hydrochloride, thiamine, thiamine monophosphate, thiamine pyrophosphate, paracetamol, guanidine hydrochloride and quinine hydrochloride. The formulations according to the invention show a reduced viscosity and increased stability of the respective protein.

The term "liquid composition" as used herein, refers to a aqueous protein solution at least containing a viscosity reducing excipient.

The term "liquid formulation" as used herein, refers to a liquid composition for therapeutic use, wherein the protein is a therapeutic protein that is either supplied in an acceptable pharmaceutical diluent or one that is reconstituted in an acceptable pharmaceutical diluent prior to administration to the patient.

In a preferred embodiment, the protein contained in the compositions and formulations according to the invention is a therapeutic protein.

The term "therapeutic proteins" as used herein refers to any protein or polypeptide that is administered to a subject with the aim of treating or preventing a disease or medical condition. In particular, the subject may be a mammal or a human.

Therapeutic proteins can be administered for different purposes, such as replacing a protein that is deficient or abnormal, augmenting an existing pathway, providing a novel function or activity, interfering with a molecule or organism and delivering other compounds or proteins, such as a radionuclide, cytotoxic drug, or effector proteins. Therapeutic proteins encompass antibody-based drugs, Fc fusion proteins, anticoagulants, blood factors, bone morphogenetic proteins, engineered protein scaffolds, enzymes, growth factors, hormones, interferons, interleukins, antibody drug conjugates (ADCs) and thrombolytics. Therapeutic proteins can be naturally occurring proteins or recombinant proteins. Their sequence can be natural or engineered.

In a particularly preferred embodiment, the protein in the compositions and formulations according to the invention is an antibody, in particular a therapeutic antibody.

In a further particularly preferred embodiment, the protein in the compositions and formulations according to the invention is a plasma derived protein, in particular IgG or hyperIgG. Some pharmaceutical formulations containing plasma proteins comprise of mixtures of different plasma proteins.

The term "plasma derived proteins" herein refers to a protein derived from the blood plasma of a donor by plasma fractionation. Said donor can be human or non-human. One example for plasma proteins are immune globulines.

The term "IgG" herein refers to an Immune globbuline type G. The term "IgM" herein refers to an Immune globbuline type M. The term "IgA" herein refers to an Immune globbuline type A.

The term "hyper-IgG" herein refers to a formulation of IgGs purified from a donor that has been infected by or vaccinated against a specific disease. Said donor can be human or non-human.

The term "antibody" herein refers to monoclonal antibodies (including full length or intact monoclonal antibodies), polyclonal antibodies, multivalent antibodies, multispecific antibodies (e.g., bispecific antibodies), and antibody fragments.

Antibody fragments comprise only a portion of an intact antibody, generally including an antigen binding site of the intact antibody and thus retaining the ability to bind antigen. Examples of antibody fragments encompassed by the present definition include: Fab fragments, Fab' fragments, Fd fragments, Fd' fragments, Fv fragments, dAb fragments, isolated CDR regions, F(ab')2 fragments as well as single chain antibody molecules, diabodies and linear antibodies.

In one embodiment, the protein is a biosimilar. A "biosimilar" is herein defined as a biological medicine that is highly similar to another already approved biological medicine. In a preferred embodiment, the biosimilar is a monoclonal antibody.

In one embodiment, the compositions and formulations according to the invention comprise more than one protein species.

The compositions and formulations according to the invention comprise a first viscosity reducing excipient selected from the group consisting of cyanocobalamin (CAS-Registry Number 68-19-9), pyridoxine (vitamin $B_6$, CAS-Registry Number 65-23-6), ascorbic acid (vitamin C, CAS-Registry Number 50-81-7), folic acid (CAS-Registry Number 59-30-3), thiamine monophosphate (CAS-Registry Number 10023-48-0), thiamine pyrophosphate (cocarboxylase, CAS-Registry Number 154-87-0), paracetamol (acetaminophen, CAS-Registry Number 103-90-2), guanidine hydrochloride (carbamimidoylazanium chloride, CAS-Registry Number 50-01-1) and quinine hydrochloride ((R)-[(1S, 2S,4S,5R)-5-ethenyl-1-azabicyclo[2.2.2]octan-2-yl](6-methoxyquinolin-4-yl)methanol dihydrate hydrochloride, CAS-Registry Number 6119-47-7).

According to the invention, the viscosity reducing excipient also include salts or solvates of the excipients. Preferred salts in the context of the present invention are physiologically acceptable salts of the compounds according to the invention. Salts which are not themselves suitable for pharmaceutical uses but can be used, for example, for isolation, purification or storage of the compounds according to the invention are also included.

Physiologically acceptable salts of the compounds according to the invention include salts of conventional bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 C atoms, such as, by way of example and preferably, ethylamine, diethylamine, triethylamine, N,N-diisopropylethylamine, monoethanolamine, diethanolamine, triethanolamine, dimethylaminoethanol, diethylaminoethanol, procaine, dicyclohexylamine, dibenzylamine, N-methylpiperidine, N-methylmorpholine, arginine, lysine and 1,2-ethylenediamine.

Physiologically acceptable salts of the compounds according to the invention include salts of conventional acids, such as, by way of example and preferably, acetate, adipate, alginate, citrate, aspartate, benzoate, benzenesulfonate, bisulfate, butyrate, camphorate, camphorsulfonate, carbonate, digluconate, glycerophosphate, hemisulfate, heptanoate, hexanoate, formate, fumarate, hydrochloride, hydrobromide, hydroiodide, 2-hy-droxyethansulfonate (isethionate), lactate, maleate, mesitylenesulfonate, methanesulfonate, naphthyl-enesulfonate, nicotinate, 2-naphthalenesulfonate, oxalate, pamoate, pectinate, persulfate, 3-phenylpropri-onate, picrate, pivalate, propionate, succinate, sulfate, tartrate, trichloroacetate, trifluoroacetate, phos-phate, glutamate, bicarbonate, para-toluenesulfonate, and undecanoate.

Without being limited to specific examples, physiologically acceptable salts can be salts of folic acid, e.g. sodium folate, salts of ascorbic acid, e.g. sodium ascorbate, salts of thiamine, e.g. thiamine hydrochloride, salts of ornithine, e.g. ornithine monohydrochloride or salts of carnithine, e.g. carnitine hydrochloride.

Solvates in the context of the invention are designated as those forms of the compounds according to the invention which form a complex in the solid or liquid state by coordination with solvent molecules. Hydrates are a specific form of solvates, in which the coordination takes place with water. Hydrates are preferred solvates in the context of the present invention.

In one embodiment, the invention comprises at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol.

The liquid compositions and formulations according to the invention comprise an amount of the first excipient sufficient to reduce the viscosity of the composition and/or stabilize the protein. For example, the compositions and formulations according to the invention may comprise about 5 mM to about 300 mM, about 5 mM to about 250 mM or about 5 mM to about 150 mM of the first excipient. In exemplary embodiments the concentration of the first excipient is 1, 5, 10, 12, 13, 15, 20, 25, 30, 35, 50, 75, 100, 105, 110, 115, 120, 125, 130, 135, 140, 145, 150, 155, 160, 165, 170, 175, 180, 185, 190, 195, 200, 210, 220, 250, or 300 mM or greater.

In a preferred embodiment, the compositions according to the invention comprise 1 to 9 mM of cyanocobalamin, more preferably 5 mM. In another preferred embodiment, the compositions according to the invention comprise 5 to 500 mM of pyridoxine, more preferably 25 to 300 mM, most preferably 150 mM when used alone and 75 mM when used in combination. In another preferred embodiment, the compositions according to the invention comprise 5 to 500 mM of ascorbic acid, more preferably 25 to 300 mM, most preferably 150 mM. In a preferred embodiment, the compositions according to the invention comprise 5 to 20 mM of folic acid, more preferably 5 to 15 mM, most preferably 13 mM when used alone and 12 mM when used in combination. In another preferred embodiment, the compositions according to the invention comprise 1 to 420 mM of thiamine monophosphate, more preferably 25 to 300 mM, most preferably 150 mM when used alone and 75 mM when used in combination. In another preferred embodiment, the compositions according to the invention comprise 1 to 450 mM of thiamine pyrophosphate, more preferably 25 to 300 mM, most preferably 75 mM. In another preferred embodiment, the compositions according to the invention comprise 5 to 500 mM of guanidine hydrochloride, more preferably 25 to 300 mM, most preferably 150 mM. In another preferred embodiment, the compositions according to the invention comprise 1 to 25 mM of quinine hydrochloride, more preferably 5 to 25 mM, most preferably 25 mM. In another preferred embodiment, the compositions according to the invention comprise 5 to 100 mM of paracetamol, more preferably 25 to 100 mM, most preferably 75 mM.

The inventors have surprisingly found that the addition of valine, proline, leucine, isoleucine, phenylalanine, cyanocobalamin, pyridoxine, ascorbic acid, folic acid, thiamine hydrochloride, thiamine, thiamine monophosphate, thiamine pyrophosphate, paracetamol, guanidine hydrochloride or quinine hydrochloride significantly reduces the viscosity of a protein solution and increases the stability of said protein in the solution. The present invention thus provides compositions and formulations having reduced viscosity and/or increased stability.

The liquid compositions and formulations according to the invention show an increased stability in comparison to a composition comprising a protein, but not comprising the first and/or second excipient.

Cyanocobalamin, pyridoxine, ascorbic acid, folic acid, thiamine, thiamine monophosphate, thiamine pyrophosphate, guanidine hydrochloride, quinine hydrochloride and paracetamol are all compounds known to be non-toxic and safe. Thus, their administration is well tolerated.

In one aspect of the invention these compositions and formulations may further comprise excipients that are used for purposes other than reducing viscosity, e.g. stabilization, solubilization or preservation.

In another aspect of the invention, the compositions and formulations comprise more than one of the first excipients. For example, the compositions and formulations according to the invention may comprise two, three or four of the first excipients, preferably they contain two of the first excipients.

The combination of two, three or four first excipients can synergically reduce the viscosity and/or increase stability in the compositions and formulations comprising a protein or in protein solutions. As defined herein, "synergically" refers to the effect that the action of a combination of components is greater than the sum of the action of each of the components alone.

In one embodiment, the compositions and formulations of the invention comprise cyanocobalamine and pyridoxine. In one embodiment, the compositions and formulations of the invention comprise cyanocobalamine and ascorbic acid. In one embodiment, the compositions and formulations of the invention comprise cyanocobalamine and folic acid. In one embodiment, the compositions and formulations of the invention comprise cyanocobalamine and thiamine monophosphate. In one embodiment, the compositions and formulations of the invention comprise cyanocobalamine and thiamine pyrophosphate. In one embodiment, the compositions and formulations of the invention comprise cyanocobalamine and guanidine hydrochloride. In one embodiment, the compositions and formulations of the invention comprise cyanocobalamine and quinine hydrochloride. In one embodiment, the compositions and formulations of the invention comprise cyanocobalamine and paracetamol.

In one embodiment, the compositions and formulations of the invention comprise pyridoxine and ascorbic acid. In one embodiment, the compositions and formulations of the invention comprise pyridoxine and folic acid. In one embodiment, the compositions and formulations of the invention comprise pyridoxine and thiamine monophosphate. In one embodiment, the compositions and formulations of the invention comprise pyridoxine and thiamine pyrophosphate. In one embodiment, the compositions and formulations of the invention comprise pyridoxine and guanidine hydrochloride. In one embodiment, the compositions and formulations of the invention comprise pyridoxine and quinine hydrochloride. In one embodiment, the compositions and formulations of the invention comprise pyridoxine and paracetamol.

In one embodiment, the compositions and formulations of the invention comprise ascorbic acid and folic acid. In one embodiment, the compositions and formulations of the invention comprise ascorbic acid and thiamine monophosphate. In one embodiment, the compositions and formulations of the invention comprise ascorbic acid and thiamine pyrophosphate. In one embodiment, the compositions and formulations of the invention comprise ascorbic acid and guanidine hydrochloride. In one embodiment, the compositions and formulations of the invention comprise ascorbic acid and quinine hydrochloride. In one embodiment, the compositions and formulations of the invention comprise ascorbic acid and paracetamol.

In one embodiment, the compositions and formulations of the invention comprise folic acid and thiamine monophosphate. In one embodiment, the compositions and formulations of the invention comprise folic acid and thiamine pyrophosphate. In one embodiment, the compositions and formulations of the invention comprise folic acid and guanidine hydrochloride. In one embodiment, the compositions and formulations of the invention comprise folic acid and quinine hydrochloride. In one embodiment, the compositions and formulations of the invention comprise folic acid and paracetamol.

In one embodiment, the compositions and formulations of the invention comprise thiamine monophosphate and thiamine pyrophosphate. In one embodiment, the compositions and formulations of the invention comprise thiamine monophosphate and guanidine hydrochloride. In one embodiment, the compositions and formulations of the invention comprise thiamine monophosphate and quinine hydrochloride. In one embodiment, the compositions and formulations of the invention comprise thiamine monophosphate and paracetamol.

In one embodiment, the compositions and formulations of the invention comprise thiamine pyrophosphate and guanidine hydrochloride. In one embodiment, the compositions and formulations of the invention comprise thiamine pyrophosphate and quinine hydrochloride. In one embodiment, the compositions and formulations of the invention comprise thiamine pyrophosphate and paracetamol.

In one embodiment, the compositions and formulations of the invention comprise guanidine hydrochloride and quinine hydrochloride. In one embodiment, the compositions and formulations of the invention comprise guanidine hydrochloride and paracetamol.

In one embodiment, the compositions and formulations of the invention comprise quinine hydrochloride and paracetamol.

In a preferred embodiment, the compositions and formulations of the invention comprise phenylalanine and an excipient selected from the group consisting of pyridoxine, ascorbic acid, folic acid, thiamine hydrochloride, thiamine monophosphate and thiamine pyrophosphate. In a preferred embodiment, the compositions and formulations of the invention comprise thiamine hydrochloride and an excipient selected from the group consisting of pyridoxine or folic acid. A combination of these excipients is particularly useful for reducing the viscosity of a protein solution or composition.

In one embodiment, the compositions and formulations of the invention comprise is thiamine hydrochloride and folic acid. In one embodiment, the compositions and formulations of the invention comprise thiamine hydrochloride and pyridoxine. In one embodiment, the compositions and formulations of the invention comprise phenylalanine and pyridoxine. In one embodiment, the compositions and formulations of the invention comprise phenylalanine and thiamine monophosphate.

In one embodiment, the compositions and formulations of the invention comprise phenylalanine and thiamine pyrophosphate. In one embodiment, the compositions and formulations of the invention comprise phenylalanine and folic acid.

When more than one excipient is present in the compositions and formulations of the invention, the concentration of the excipients may be the same or different.

The compositions and formulations according to the invention may further comprise at least one second viscosity reducing excipient.

The term "viscosity reducing excipient", as used herein, refers to any compound at a suitable concentration which is known to reduce the viscosity of a protein solution by at least 5% compared to an identical composition not comprising the viscosity reducing excipient.

The at least one second viscosity reducing excipient is preferably selected from the group consisting of valine (CAS-Registry Number 72-18-4), proline (CAS-Registry Number 147-85-3), leucine (CAS-Registry Number 61-90-5), isoleucine (CAS-Registry Number 73-32-5), phenylalanine (CAS-Registry Number 63-91-2), thiamine hydrochloride (CAS-Registry Number 67-03-8), arginine, ornithine, carnitine, meglumine ((2R,3R,4R,5S)-6-(methylamino) hexane-1,2,3,4,5-pentol, CAS-Registry Number 6284-40-8), benzenesulfonic acid (CAS-Registry Number 98-11-3), caffeine (1,3,7-Trimethylxanthine, CAS-Registry Number 58-08-2) and camphorsulfonic acid ((7,7-dimethyl-2-oxobicyclo[2.2.1]heptan-1-yl)methanesulfonic acid.

The liquid compositions and formulations according to the invention may comprise an amount of at least one second excipient selected from the group consisting of valine, proline, leucine, isoleucine, phenylalanine, arginine, ornithine, carnitine, meglumine, camphorsulfonic acid and benzenesulfonic acid sufficient to further reduce the viscosity of the composition and/or stabilize the protein. For example, the compositions and formulations according to the invention may comprise about 50 mM to about 300 mM, about 100 mM to about 250 mM or about 140 mM to about 200 mM of the second excipient selected from the group consisting of valine, proline, leucine, isoleucine, phenylalanine, arginine, ornithine, carnitine, meglumine, camphorsulfonic acid and benzenesulfonic acid. In exemplary embodiments the concentration of the at least one second excipient selected from the group consisting of valine, proline, leucine, isoleucine, phenylalanine, arginine, ornithine, carnitine, meglumine, camphorsulfonic acid and benzenesulfonic acid is 5, 10, 15, 20, 25, 30, 35, 50, 75, 100, 105, 110, 115, 120, 125, 130, 135, 140, 145, 150, 155, 160, 165, 170, 175, 180, 185, 190, 195, 200, 210, 220, 250, or 300 mM or greater. In a preferred embodiment, the compositions according to the invention comprise 150 mM of valine, leucine, isoleucine, proline, phenylalanine, lysine or thiamine hydrochloride. In a preferred embodiment, the compositions and formulations according to the invention comprise 50-100 mM of the second excipient selected from the group consisting of valine, proline, leucine, isoleucine, phenylalanine, arginine, ornithine, carnitine, meglumine, camphorsulfonic acid and benzenesulfonic acid.

In another preferred embodiment the compositions and formulations according to the invention comprise folic acid in a concentration of 5-13 mM. In another preferred embodiment the compositions and formulations according to the invention comprise cyanocobalamin in a concentration of 5 mM.

In these embodiments, the first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol forms a viscosity-reducing solution together with the second excipient selected from the group consisting of valine, proline, leucine, isoleucine, phenylalanine, arginine, ornithine, carnitine, meglumine, camphorsulfonic acid and benzenesulfonic acid that can be added to compositions and formulations comprising a protein or protein solutions in order to reduce the viscosity and/or increase stability thereof.

In another preferred embodiment the compositions and formulations according to the invention comprise at least one first and at least one second viscosity reducing excipient, wherein the excipients synergistically reduce the viscosity and/or increase stability in the compositions and formulations comprising a protein or in protein solutions.

According to the invention, a synergistical reduction of the viscosity is given if the viscosity reduction by a combination of two or more excipients is more than the expected sum of the viscosity reduction of each individual excipient. Preferably a synergistical reduction of the viscosity is given if the percentage viscosity reduction by a combination of two or more excipients is more than the expected sum of the percentage viscosity reduction of each individual excipient.

Additionally, according to the invention, a combination of two or more viscosity reducing excipients is synergistic in case the protein stability reduction by a combination of two or more excipients is less than the expected sum of the stability reduction of each individual excipient.

In one embodiment all combinations mentioned in the present application result in a synergistic reduction of viscosity of a liquid composition comprising a protein.

In one embodiment the following combinations pyridoxine/arginine, folic acid/ornithine, folic acid/carnithine, pyridoxine/meglumine, thiamine monophosphate/meglumine, pyridoxine/thiamine monophosphate, phenylalanine/camphorsulfonic acid and phenylalanine/benzenesulfonic acid result in a synergistic reduction of viscosity of a liquid composition comprising a protein.

In one embodiment, the compositions and formulations of the invention comprise cyanocobalamin and arginine. In one embodiment, the compositions and formulations of the invention comprise cyanocobalamin and ornithine. In one embodiment, the compositions and formulations of the invention comprise cyanocobalamin and carnitine. In one embodiment, the compositions and formulations of the invention comprise cyanocobalamin and meglumine. In one embodiment, the compositions and formulations of the invention comprise cyanocobalamin and camphorsulfonic acid. In one embodiment, the compositions and formulations of the invention comprise cyanocobalamin and benzenesulfonic acid. In one embodiment, the compositions and formulations of the invention comprise cyanocobalamin and caffeine. In one embodiment, the compositions and formulations of the invention comprise cyanocobalamin and valine. In one embodiment, the compositions and formulations of the invention comprise cyanocobalamin and proline. In one embodiment, the compositions and formulations of the invention comprise cyanocobalamin and leucine. In one embodiment, the compositions and formulations of the invention comprise cyanocobalamin and isoleucine. In one embodiment, the compositions and formulations of the invention comprise cyanocobalamin and phenylalanine. In one embodiment, the compositions and formulations of the invention comprise cyanocobalamin and thiamin hydrochloride.

In one embodiment, the compositions and formulations of the invention comprise pyridoxine and arginine. In one embodiment, the compositions and formulations of the invention comprise pyridoxine and ornithine. In one embodiment, the compositions and formulations of the invention comprise pyridoxine and carnitine. In one embodiment, the compositions and formulations of the invention comprise pyridoxine and meglumine. In one embodiment, the compositions and formulations of the invention comprise pyridoxine and camphorsulfonic acid. In one embodiment, the compositions and formulations of the invention comprise pyridoxine and benzenesulfonic acid. In one embodiment, the compositions and formulations of the invention comprise pyridoxine and caffeine. In one embodiment, the compositions and formulations of the invention comprise pyridoxine and valine. In one embodiment, the compositions and formulations of the invention comprise pyridoxine and proline. In one embodiment, the compositions and formulations of the invention comprise pyridoxine and leucine. In one embodiment, the compositions and formulations of the invention comprise pyridoxine and isoleucine. In one embodiment, the compositions and formulations of the invention comprise pyridoxine and phenylalanine. In one embodiment, the compositions and formulations of the invention comprise pyridoxine and thiamin hydrochloride.

In one embodiment, the compositions and formulations of the invention comprise ascorbic acid and arginine. In one embodiment, the compositions and formulations of the invention comprise ascorbic acid and ornithine. In one embodiment, the compositions and formulations of the invention comprise ascorbic acid and carnitine. In one embodiment, the compositions and formulations of the invention comprise ascorbic acid and meglumine. In one embodiment, the compositions and formulations of the invention comprise ascorbic acid and camphorsulfonic acid. In one embodiment, the compositions and formulations of the invention comprise ascorbic acid and benzenesulfonic acid. In one embodiment, the compositions and formulations of the invention comprise ascorbic acid and caffeine. In one embodiment, the compositions and formulations of the invention comprise ascorbic acid and valine. In one embodiment, the compositions and formulations of the invention comprise ascorbic acid and proline. In one embodiment, the compositions and formulations of the invention comprise ascorbic acid and leucine. In one embodiment, the compositions and formulations of the invention comprise ascorbic acid and isoleucine. In one embodiment, the compositions and formulations of the invention comprise ascorbic acid and phenylalanine. In one embodiment, the compositions and formulations of the invention comprise ascorbic acid and thiamin hydrochloride.

In one embodiment, the compositions and formulations of the invention comprise folic acid and arginine. In one embodiment, the compositions and formulations of the invention comprise folic acid and ornithine. In one embodiment, the compositions and formulations of the invention comprise folic acid and carnitine. In one embodiment, the compositions and formulations of the invention comprise folic acid and meglumine. In one embodiment, the compositions and formulations of the invention comprise folic acid and camphorsulfonic acid. In one embodiment, the compositions and formulations of the invention comprise folic acid and benzenesulfonic acid. In one embodiment, the compositions and formulations of the invention comprise folic acid and caffeine. In one embodiment, the compositions and formulations of the invention comprise folic acid and valine. In one embodiment, the compositions and formulations of the invention comprise folic acid and proline. In one embodiment, the compositions and formulations of the invention comprise folic acid and leucine. In one embodiment, the compositions and formulations of the invention comprise folic acid and isoleucine. In one embodiment, the compositions and formulations of the invention comprise folic acid and phenylalanine. In one embodiment, the compositions and formulations of the invention comprise folic acid and thiamin hydrochloride.

In one embodiment, the compositions and formulations of the invention comprise thiamine monophosphate and arginine. In one embodiment, the compositions and formulations of the invention comprise thiamine monophosphate and ornithine. In one embodiment, the compositions and formulations of the invention comprise thiamine monophosphate and carnitine. In one embodiment, the compositions and formulations of the invention comprise thiamine monophosphate and meglumine. In one embodiment, the compositions and formulations of the invention comprise thiamine monophosphate and camphorsulfonic acid. In one embodiment, the compositions and formulations of the invention comprise thiamine monophosphate and benzenesulfonic acid. In one embodiment, the compositions and formulations of the invention comprise thiamine monophosphate and caffeine. In one embodiment, the compositions and formulations of the invention comprise thiamine monophosphate and valine. In one embodiment, the compositions and formulations of the invention comprise thiamine monophosphate and proline. In one embodiment, the compositions and formulations of the invention comprise thiamine monophosphate and leucine. In one embodiment, the compositions and formulations of the invention comprise thiamine monophosphate and isoleucine. In one embodiment, the compositions and formulations of the invention comprise thiamine monophosphate and phenylalanine. In one embodiment, the compositions and formulations of the invention comprise thiamine monophosphate and thiamin hydrochloride.

In one embodiment, the compositions and formulations of the invention comprise thiamine pyrophosphate and arginine. In one embodiment, the compositions and formulations of the invention comprise thiamine pyrophosphate and ornithine. In one embodiment, the compositions and formulations of the invention comprise thiamine pyrophosphate and carnitine. In one embodiment, the compositions and formulations of the invention comprise thiamine pyrophosphate and meglumine. In one embodiment, the compositions and formulations of the invention comprise thiamine pyrophosphate and camphorsulfonic acid. In one embodiment, the compositions and formulations of the invention comprise thiamine pyrophosphate and benzenesulfonic acid. In one embodiment, the compositions and formulations of the invention comprise thiamine pyrophosphate and caffeine. In one embodiment, the compositions and formulations of the invention comprise thiamine pyrophosphate and valine. In one embodiment, the compositions and formulations of the invention comprise thiamine pyrophosphate and proline. In one embodiment, the compositions and formulations of the invention comprise thiamine pyrophosphate and leucine. In one embodiment, the compositions and formulations of the invention comprise thiamine pyrophosphate and isoleucine. In one embodiment, the compositions and formulations of the invention comprise thiamine pyrophosphate and phenylalanine. In one embodiment, the compositions and formulations of the invention comprise thiamine pyrophosphate and thiamin hydrochloride.

In one embodiment, the compositions and formulations of the invention comprise guanidine hydrochloride and arginine. In one embodiment, the compositions and formulations of the invention comprise guanidine hydrochloride and ornithine. In one embodiment, the compositions and formulations of the invention comprise guanidine hydrochloride and carnitine. In one embodiment, the compositions and formulations of the invention comprise guanidine hydrochloride and meglumine. In one embodiment, the compositions and formulations of the invention comprise guanidine hydrochloride and camphorsulfonic acid. In one embodiment, the compositions and formulations of the invention comprise guanidine hydrochloride and benzenesulfonic acid. In one embodiment, the compositions and formulations of the invention comprise guanidine hydrochloride and caffeine. In one embodiment, the compositions and formulations of the invention comprise guanidine hydrochloride and valine. In one embodiment, the compositions and formulations of the invention comprise guanidine hydrochloride and proline. In one embodiment, the compositions and formulations of the invention comprise guanidine hydrochloride and leucine. In one embodiment, the compositions and formulations of the invention comprise guanidine hydrochloride and isoleucine. In one embodiment, the compositions and formulations of the invention comprise guanidine hydrochloride and phenylalanine. In one embodiment, the compositions and formulations of the invention comprise guanidine hydrochloride and thiamin hydrochloride.

In one embodiment, the compositions and formulations of the invention comprise quinine hydrochloride and arginine. In one embodiment, the compositions and formulations of the invention comprise quinine hydrochloride and ornithine. In one embodiment, the compositions and formulations of the invention comprise quinine hydrochloride and carnitine. In one embodiment, the compositions and formulations of the invention comprise quinine hydrochloride and meglumine. In one embodiment, the compositions and formulations of the invention comprise quinine hydrochloride and camphorsulfonic acid. In one embodiment, the compositions and formulations of the invention comprise quinine hydrochloride and benzenesulfonic acid. In one embodiment, the compositions and formulations of the invention comprise quinine hydrochloride and caffeine. In one embodiment, the compositions and formulations of the invention comprise quinine hydrochloride and valine. In one embodiment, the compositions and formulations of the invention comprise quinine hydrochloride and proline. In one embodiment, the compositions and formulations of the invention comprise quinine hydrochloride and leucine. In one embodiment, the compositions and formulations of the invention comprise quinine hydrochloride and isoleucine. In one embodiment, the compositions and formulations of the invention comprise quinine hydrochloride and phenylalanine. In one embodiment, the compositions and formulations of the invention comprise quinine hydrochloride and thiamin hydrochloride.

In one embodiment, the compositions and formulations of the invention comprise paracetamol and arginine. In one embodiment, the compositions and formulations of the invention comprise paracetamol and ornithine. In one embodiment, the compositions and formulations of the invention comprise paracetamol and carnitine. In one embodiment, the compositions and formulations of the invention comprise paracetamol and meglumine. In one embodiment, the compositions and formulations of the invention comprise paracetamol and camphorsulfonic acid. In one embodiment, the compositions and formulations of the invention comprise paracetamol and benzenesulfonic acid. In one embodiment, the compositions and formulations of the invention comprise paracetamol and caffeine. In one embodiment, the compositions and formulations of the invention comprise paracetamol and valine. In one embodiment, the compositions and formulations of the invention comprise paracetamol and proline. In one embodiment, the compositions and formulations of the invention comprise paracetamol and leucine. In one embodiment, the compositions and formulations of the invention comprise paracetamol and isoleucine. In one embodiment, the compositions and formulations of the invention comprise paracetamol and phenylalanine. In one embodiment, the compositions and formulations of the invention comprise paracetamol and thiamin hydrochloride.

In a preferred embodiment, the compositions and formulations according to the invention are liquid formulations. In a preferred embodiment, the compositions and formulations according to the invention are liquid formulations and the protein is a therapeutic protein.

In another aspect, the invention provides lyophilized protein formulations comprising a protein and at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. Upon reconstitution with a suitable amount of diluent, the formulations exhibit reduced viscosity relative to control formulations with the otherwise same composition but not comprising the excipient. Thus, the excipient is present at an amount effective to reduce viscosity upon reconstitution with diluent.

In another aspect, the invention provides lyophilized protein formulations comprising a protein and at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and at least one second viscosity reducing excipient selected from the group consisting of valine, proline, leucine, isoleucine, phenylalanine, arginine, ornithine, carnitine, meglumine, camphorsulfonic acid and benzenesulfonic acid.

A lyophilized protein formulation includes a protein and the at least one excipient according to the invention that has been dried and is present as particles in, for example, powder form. In the present context the expression "powder" refers to a collection of essentially dry particles, i.e. the moisture content being at least below about 10% by weight, 6% by weight, 4% by weight, or lower.

As defined herein, "viscosity" refers to the resistance of a substance (typically a liquid) to flow. Viscosity is related to the concept of shear force; it can be understood as the effect of different layers of the fluid exerting shearing force on each other, or on other surfaces, as they move against each other. There are several ways to express viscosity. The units of viscosity are $Ns/m^2$, known as Pascal-seconds (Pas). Viscosity can be "kinematic" or "absolute". Kinematic viscosity is a measure of the rate at which momentum is transferred through a fluid. It is measured in Stokes (St). The kinematic viscosity is a measure of the resistive flow of a fluid under the influence of gravity. When two fluids of equal volume and differing viscosity are placed in identical capillary viscometers and allowed to flow by gravity, the more viscous fluid takes longer than the less viscous fluid to flow through the capillary. If, for example, one fluid takes 200 seconds (s) to complete its flow and another fluid takes 400 s, the second fluid is called twice as viscous as the first on a kinematic viscosity scale. The dimension of kinematic viscosity is $length^2/time$. Commonly, kinematic viscosity is expressed in centiStokes (cSt). The SI unit of kinematic viscosity is $mm^2/s$, which is equal to 1 cSt. The "absolute viscosity," sometimes called "dynamic viscosity" or "simple viscosity," is the product of kinematic viscosity and fluid density. Absolute viscosity is expressed in units of centipoise (cP). The SI unit of absolute viscosity is the milliPascal-second (mPas), where 1 cP=1 mPas.

Viscosity may be measured by using, for example, a viscometer at a given shear rate or multiple shear rates. An "extrapolated zero-shear" viscosity can be determined by creating a best fit line of the four highest-shear points on a plot of absolute viscosity versus shear rate, and linearly extrapolating viscosity back to zero-shear. Alternatively, for a Newtonian fluid, viscosity can be determined by averaging viscosity values at multiple shear rates. Viscosity can also be measured using a microfluidic viscometer at single or multiple shear rates (also called flow rates), wherein absolute viscosity is derived from a change in pressure as a liquid flows through a channel. Viscosity equals shear stress over shear rate. Viscosities measured with microfluidic viscometers can, in some embodiments, be directly compared to extrapolated zero-shear viscosities, for example those extrapolated from viscosities measured at multiple shear rates using a cone and plate viscometer. According to the invention, viscosity of compositions and formulations is reduced when at least one of the methods described above show a stabilizing effect. Preferably, viscosity is measured at 20° C. using a microfluidic viscometer. More preferably the viscosity is measured using a RheoSense mVROC microfluidic viscometer at 20° C. Most preferably the viscosity is measured at 20° C. using a RheoSense mVROC microfluidic viscometer and using a 500 μl syringe, a shear rate of 3000 s-1 or 2000 s-1 and a volume of 200 μl.

The person ordinary skilled in the art is familiar with the viscosity measurement using a microfluidic viscometer. As microfluidic viscometer the RheoSense mVROC microfluidic viscometer (mVROC™ Technology), especially with the parameters described above can be used. Detailed specifications, methods and setting can be found in the 901003.5.1-mVROC_User's_Manual.

"Shear rate" herein refers to the rate of change of velocity at which one layer of fluid passes over an adjacent layer. The velocity gradient is the rate of change of velocity with distance from the plates. This simple case shows the uniform velocity gradient with shear rate (v1−v2)/h in units of (cm/sec)/(cm)=1/sec. Hence, shear rate units are reciprocal seconds or, in general, reciprocal time. For a microfluidic viscometer, change in pressure and flow rate are related to shear rate. "Shear rate" is to the speed with which a material is deformed. Formulations containing proteins and viscosity-lowering agents are typically measured at shear rates ranging from about 0.5 $s^{-1}$ to about 200 $s^{-1}$ when measured using a cone and plate viscometer and a spindle appropriately chosen by one skilled in the art to accurately measure viscosities in the viscosity range of the sample of interest (i.e., a sample of 20 cP is most accurately measured on a CPE40 spindle affixed to a DV2T viscometer (Brookfield)); greater than about 20 $s^{-1}$ to about 3,000 $s^{-1}$ when measured using a microfluidic viscometer.

For classical "Newtonian" fluids, as generally used herein, viscosity is essentially independent of shear rate. For "non-Newtonian fluids," however, viscosity either decreases or increases with increasing shear rate, e.g., the fluids are "shear thinning" or "shear thickening", respectively. In the case of concentrated (i.e., high-concentration) protein solutions, this may manifest as pseudoplastic shear-thinning behavior, i.e., a decrease in viscosity with shear rate.

In one embodiment, the compositions and formulations of the invention show a reduction of viscosity of at least 5%, 10%, 15%, 20%, 25%, 30%, 35%, 40%, 45%, 50%, 55%, 60%, 65%, 70% or 75% compared to an identical composition not comprising the at least one first excipient.

In one embodiment, the compositions and formulations of the invention show a reduction of viscosity of at least 5%, 10%, 15%, 20%, 25%, 30%, 35%, 40%, 45%, 50%, 55%, 60%, 65%, 70% or 75% compared to an identical composition not comprising the at least one first and at least one second excipient.

As used herein, the term "stability" encompasses both chemical and physical stability.

The term "chemical stability" herein refers to the ability of the protein components in a formulation to resist degradation via chemical pathways, such as oxidation, deamidation or hydrolysis. A protein formulation is typically considered chemically stable if less than about 5% of the components are degraded after 24 months at 4° C. According to the present invention the protein formulation is typically considered chemically stable if less than about 5% of the components are degraded after 24 weeks at 25° C. with a relative humidity of 60%.

Stability can be assessed in many ways known to the skilled person, including monitoring conformational change over a range of temperatures (thermostability) and/or time periods (shelf-life) and/or after exposure to stressful handling situations (e.g. physical shaking). Stability of formulations containing varying concentrations of formulation components can be measured using a variety of methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including differential scanning calorimetry (DSC), e.g. to determine the temperature of denaturation, or circular dichroism (CD), which measures the molar ellipticity of the protein. Fluorescence can also be used to analyze the composition. Fluorescence encompasses the emission of light subsequent to absorption of light, which requires a suitable wavelength. Potential readouts are changes in the polar properties of light, light intensity, or emission wavelength. Fluorescence emission can be intrinsic to a protein or can be due to a fluorescence reporter molecule that for example binds to the hydrophobic pockets of partially unfolded proteins. An increase in binding of reporter molecules can be monitored by detection of the fluorescence signal of a protein sample. Other means for measuring stability can be used and are well known to persons skilled in the art. According to the invention, stability of compositions and formulations is increased when at least one of the methods described above show a stabilizing effect.

In one embodiment, the compositions and formulations of the invention show an increase in stability of the protein of at least 5%, 10%, 15%, 20%, 25%, 30%, 35%, 40%, 45%, 50%, 55%, 60%, 65%, 70% or 75% compared to compositions not comprising the at least one first viscosity reducing excipient or not comprising the at least one first and at least one second viscosity reducing excipient.

In one embodiment, the compositions and formulations according to the invention comprise a viscosity reducing excipient selected from the group consisting of valine, leucine, ascorbic acid, cyanocobalamin and proline and show an increased protein stability characterized by an elevated Tm and/or Tagg.

In one embodiment, the compositions and formulations according to the invention comprise a viscosity reducing excipient selected from the group consisting of valine, leucine, ascorbic acid, cyanocobalamin and proline and show both (i) an increased protein stability characterized by an elevated Tm and/or Tagg and (ii) a reduced viscosity.

In a preferred embodiment the compositions and formulations of the invention comprise phenylalanine, camphorsulfonic acid or benzenesulfonic acid as the second excipient.

In a preferred embodiment, the compositions and formulations of the invention comprise phenylalanine and pyridoxine. In a preferred embodiment, the compositions and formulations of the invention comprise phenylalanine and thiamine hydrochloride. In a preferred embodiment, the compositions and formulations of the invention comprise phenylalanine and folic acid. In a preferred embodiment, the compositions and formulations of the invention comprise phenylalanine and thiamine monophosphate. In a preferred embodiment, the compositions and formulations of the invention comprise phenylalanine and thiamine pyrophosphate.

In a preferred embodiment, the compositions and formulations of the invention comprise phenylalanine and arginine. In a preferred embodiment, the compositions and formulations of the invention comprise phenylalanine and ornithine. In a preferred embodiment, the compositions and formulations of the invention comprise phenylalanine and carnitine. In a preferred embodiment, the compositions and formulations of the invention comprise phenylalanine and meglumine. In a preferred embodiment, the compositions and formulations of the invention comprise phenylalanine and benzenesulfonic acid. In a preferred embodiment, the compositions and formulations of the invention comprise phenylalanine and camphorsulfonic acid.

In a preferred embodiment, the compositions and formulations of the invention comprise pyridoxine and arginine. In a preferred embodiment, the compositions and formulations of the invention comprise pyridoxine and ornithine. In a preferred embodiment, the compositions and formulations of the invention comprise pyridoxine and carnitine. In a preferred embodiment, the compositions and formulations of the invention comprise pyridoxine and meglumine. In a preferred embodiment, the compositions and formulations of the invention comprise pyridoxine and thiamine hydrochloride.

In a preferred embodiment, the compositions and formulations of the invention comprise folic acid and arginine. In a preferred embodiment, the compositions and formulations of the invention comprise folic acid and ornithine. In a preferred embodiment, the compositions and formulations of the invention comprise folic acid and carnitine. In a preferred embodiment, the compositions and formulations of the invention comprise folic acid and meglumine. In a preferred embodiment, the compositions and formulations of the invention comprise folic acid and thiamine hydrochloride.

In a preferred embodiment, the compositions and formulations of the invention comprise thiamine monophosphate and arginine. In a preferred embodiment, the compositions and formulations of the invention comprise thiamine monophosphate and ornithine. In a preferred embodiment, the compositions and formulations of the invention comprise thiamine monophosphate and carnitine. In a preferred embodiment, the compositions and formulations of the invention comprise thiamine monophosphate and meglumine.

In a preferred embodiment, the compositions and formulations of the invention comprise thiamine pyrophosphate and arginine. In a preferred embodiment, the compositions and formulations of the invention comprise thiamine pyrophosphate and carnitine. In a preferred embodiment, the compositions and formulations of the invention comprise thiamine pyrophosphate and meglumine.

In a preferred embodiment, the composition comprises a combination of two viscosity reducing excipients selected from the group consisting of phenylalanine and benzenesulfonic acid, phenylalanine and camphorsulfonic acid, thiamine hydrochloride and benzenesulfonic acid, thiamine hydrochloride and camphorsulfonic acid, pyridoxine and arginine, pyridoxine and ornithine, pyridoxine and carnitine, pyridoxine and meglumine, folic acid and arginine, folic acid and ornithine, folic acid and carnitine, folic acid and meglumine, thiamine monophosphate and arginine, thiamine monophosphate and ornithine, thiamine monophosphate and carnitine, thiamine monophosphate and meglumine, thiamine pyrophosphate and arginine, thiamine pyrophosphate and ornithine, thiamine pyrophosphate and carnitine, thiamine pyrophosphate and meglumine.

In a further embodiment, the liquid composition comprises a protein, at least one first viscosity reducing excipient selected from the group consisting of pyridoxine, folic acid, thiamine monophosphate and phenylalanine and at least one second viscosity reducing excipient selected from the group consisting of arginine, ornithine, carnitine, meglumine, camphorsulfonic acid and benzenesulfonic acid.

In a further preferred embodiment, the liquid composition comprises a combination of a first and a second viscosity reducing excipient selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

In a further preferred embodiment, the combination of a first and a second viscosity reducing excipient is pyridoxine and arginine. In a further preferred embodiment, the combination of a first and a second viscosity reducing excipient is folic acid and ornithine. In a further preferred embodiment, the combination of a first and a second viscosity reducing excipient is folic acid and carnithine. In a further preferred embodiment, the combination of a first and a second viscosity reducing excipient is pyridoxine and meglumine. In a further preferred embodiment, the combination of a first and a second viscosity reducing excipient is thiamine monophosphate and meglumine. In a further preferred embodiment, the combination of a first and a second viscosity reducing excipient is pyridoxine and thiamine monophosphate. In a further preferred embodiment, the combination of a first and a second viscosity reducing excipient is phenylalanine and camphorsulfonic acid. In a further preferred embodiment, the combination of a first and a second viscosity reducing excipient is phenylalanine and benzenesulfonic acid.

In a further preferred embodiment, the liquid composition comprises a combination of a first and a second viscosity reducing excipient selected from the list consisting of pyridoxine and arginine, pyridoxine and meglumine and pyridoxine and thiamine monophosphate.

In a further preferred embodiment, the liquid composition comprises a combination of a first and a second viscosity reducing excipient selected from the list consisting of folic acid and ornithine and folic acid and carnithine.

In a further preferred embodiment, the liquid composition comprises a combination of a first and a second viscosity reducing excipient selected from the list consisting of pyridoxine and meglumine and thiamine monophosphate and meglumine.

In a further preferred embodiment, the liquid composition comprises a combination of a first and a second viscosity reducing excipient selected from the list consisting of thiamine monophosphate and meglumine and pyridoxine and thiamine monophosphate.

In a further preferred embodiment, the liquid composition comprises a combination of a first and a second viscosity reducing excipient selected from the list consisting of phenylalanine and camphorsulfonic acid and phenylalanine and benzenesulfonic acid.

In one embodiment, the compositions and formulations according to the invention have a pH between 2 and 10, preferably between 4 and 8, more preferably between 5 and 7.2. In one embodiment, the compositions and formulations have a pH of exactly 5 or exactly 7.2.

The compositions and formulations according to the invention may additionally comprise pharmaceutically acceptable diluents, solvents, carriers, adhesives, binders, preservatives, solubilizers, surfactants, penetration enhancers, emulsifiers or bioavailability enhancers. The skilled person knows how to choose suitable additives for liquid compositions that are safe and well tolerated.

The compositions and formulations according the invention which comprise combinations of first and/or second viscosity reducing excipients may further comprise excipients that are used for purposes other than reducing viscosity, e.g. stabilization, solubilization or preservation.

In a preferred embodiment, the compositions and formulations according to the invention comprise a stabilizer such as a sugar and/or a surfactant. Suitable sugars as stabilizers are known in the literature, e.g. sucrose or trehalose. In a preferred embodiment, the sugar is sucrose. Suitable surfactants are known in the literature, e.g. polysorbate 20 or polysorbate 80 or poloxamer 188. In another preferred embodiment, the surfactant is polysorbate 80. The addition of a further stabilizers additionally enhances the stabilizing effect of the compositions according to the inventions.

The liquid compositions and formulations according to the invention comprise an amount of the first and optionally second excipient sufficient to reduce the viscosity of the composition and/or stabilize the protein. For example, the compositions and formulations according to the invention may comprise about 5 mM to about 300 mM, about 5 mM to about 250 mM or about 5 mM to about 150 mM of each first and optionally second excipient. In exemplary embodiments the concentration of each first and optionally second excipient is 1, 5, 10, 12, 13, 15, 20, 25, 30, 35, 50, 75, 100, 105, 110, 115, 120, 125, 130, 135, 140, 145, 150, 155, 160, 165, 170, 175, 180, 185, 190, 195, 200, 210, 220, 250, or 300 mM or greater. Preferably the concentration of each first and optionally second excipient is 75 or 150 mM.

In one embodiment the liquid compositions comprise a combination of two excipients, wherein the molar concentration of the excipients can be identical or different. Preferably the concentrations of each first and second excipient is between 1 mM and 200 mM, more preferably between 25 and 150 mM, most preferably between 50 and 100 mM. The molar ratio of the first and second excipient is between 1:100 and 100:1, preferably between 1:10 and 10:1, more preferably between 1:5 and 5:1, most preferably between 1:2 and 2:1. In a particular embodiment the molar concentration of the first and second excipient is identical.

The invention further provides a liquid composition according to the invention whereas the protein has a molecular weight from 120 kDa to 250 kDa, preferably from 130 kDa to 180 kDa.

In a preferred embodiment, the protein concentration in the compositions and formulations according to the invention is at least 1 mg/ml, at least 50 mg/ml, preferably at least 75 mg/ml and more preferably at least 100 mg/ml. In another preferred embodiment, the protein concentration is between 90 mg/ml and 300 mg/ml, more preferably the protein concentration is between 100 and 250 mg/ml, even more preferable between 120 and 210 mg/ml. The present invention is particularly useful for these high-concentration compositions, formulations and solutions.

The invention further provides a liquid composition according to the invention further comprising a buffer at a concentration of 10 mM to 50 mM. The buffer can be a suitable acetate- or phosphate salt and provide a pH of 5 to 7.2.

The invention further provides a liquid composition according to the invention further comprising a sugar as stabilizer, preferably 50 to 100 mg/ml sucrose.

The invention further provides a liquid composition according to the invention further comprising a surfactant, preferably 0.01 to 0.2 mg/ml, more preferably 0.05 mg/ml of polysorbate 80.

The invention further provides a liquid composition according to the invention whereas the viscosity is between 1 mPas and 60 mPas, preferably between 1 mPas and 50 mPas, more preferably between 1 mPas and 30 mPas, most preferably between 1 mPas and 20 mPas. Preferably the viscosity is measured at 20° C., using a microfluidic viscometer. More preferably the viscosity is measured using a RheoSense mVROC microfluidic viscometer at 20° C. Most preferably the viscosity is measured using a RheoSense mVROC microfluidic viscometer at 20° C., using a 500 μl syringe, a shear rate of 3000 s-1 or 2000 s-1 and a volume of 200 μl.

The invention further provides a liquid composition according to the invention whereas the protein has a molecular weight from 120 kDa to 250 kDa at a concentration between 90 mg/ml to 300 mg/ml, preferably further comprising an acetate buffer or phosphate buffer at a concentration between 10 mM to 50 mM, wherein the formulation has a pH between 5 and 7.2, and a viscosity between 1 mPas and 60 mPas when measured at 20° C., preferably using a microfluidic viscometer, more preferably using a RheoSense mVROC microfluidic viscometer at 20° C., most preferably using a RheoSense mVROC microfluidic viscometer at 20° C. with a 500 μl syringe, a shear rate of 3000 s-1 or 2000 s-1 and a volume of 200 μl.

Preferably, liquid composition according to the invention wherein a first and a second viscosity reducing excipient are present, have a protein concentration between 90 mg/ml to 300 mg/ml, more preferably between 100 mg/ml and 200 mg/ml and a concentration of the first and second viscosity reducing excipient between 50 and 200 mM each, more preferably between 50 and 100 mM each, most preferably 75 mM each. Preferably the protein is an antibody and has a molecular weight from 120 kDa to 250 kDa. Preferably the formulation has a pH between 4 and 8, more preferably between 5 and 7.2 and the viscosity is between 1 mPas and 60 mPas when measured at 20° C. using a microfluidic viscometer.

The invention further provides a liquid composition according to the invention whereas the protein is Infliximab. Preferably the Infliximab concentration in the liquid compositions is between 122 mg/ml and 185 mg/ml.

Infliximab (REMICADE®) developed by Janssen Biotech, Inc. and its biosimilar drugs (FUXABI®) developed by Biogen, (Inflectra) by Celltrion, is used in treatment of rheumatoid arthritis, adult ulcerative colitis, plaque psoriasis, psoriatic arthritis, ankylosing spondylitis, adult & pediatric Crohn's disease (Dose/Dosage: 5 mg/kg). Infliximab is a mAb against tumor necrosis factor alpha (TNF-α) used to treat autoimmune diseases. Infliximab neutralizes the biological activity of TNFa by binding with high affinity to the soluble and transmembrane forms of TNFa and inhibits binding of TNFa with its receptors. It is marketed under the trade name REMICADE® by Janssen Global Services, LLC ("Janssen") in the U.S., Mitsubishi Tanabe Pharma in Japan, Xian Janssen in China, and Merck Sharp & Dohme ("MSD"); elsewhere. In some embodiments, the formulations contain a biosimilar of REMICADE®, such as REMSIMA™ or INFLECTRA™. Both REMSIMA™ developed by Celltrion, Inc. ("Celltrion"), and INFLECTRA™, developed by Hospira Inc., UK. Infliximab is currently administered via iv infusion at doses ranging from about 3 mg/kg to about 10 mg/kg.

The invention further provides a liquid composition according to the invention whereas the protein is Evolocumab. Preferably the Evolocumab concentration in the liquid compositions is between 163 mg/ml and 204 mg/ml.

Evolocumab (REPATHA®) developed by Amgen is used in treatment of HeFH, CVD, reducing of low density lipoprotein cholesterol (LDL-C) by targeting PCSK9 (proprotein convertase subtilisin kexin type 9) (Dose/Dosage: 420 mg monthly). The invention further provides a kit comprising compositions and formulations according to the invention. The kit may additionally comprise instructions for administration as well as a container, a syringe and/or other device for administration.

The invention is also directed to a kit comprising a lyophilized protein formulation of the invention, optionally in a container, and instructions for its reconstitution and administration, optionally with a vial of sterile diluent, and optionally with a syringe or other administration device. Exemplary containers include vials, tubes, bottles, single or multi-chambered pre-filled syringes, or cartridges, but also a 96-well plate comprising ready-to-use freeze-dried or spray-dried formulations sitting in the wells. Exemplary administration devices include syringes with or without needles, infusion pumps, jet injectors, pen devices, transdermal injectors, or other needle-free injectors.

The invention is also directed to methods for reducing the viscosity of a protein solution for the purpose of the manufacture of all aforementioned liquid compositions and formulations. All embodiments regarding the combinations and concentrations of excipients, proteins, concentrations and molecular weight of proteins, pH, buffer and buffer concentrations as mentioned for the liquid composition above are also applicable for the methods for reducing the viscosity of a protein solution.

The invention further provides a method for reducing the viscosity of a protein solution comprising a step of adding at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof to the protein solution.

The invention further provides a method for reducing the viscosity of a protein solution comprising a step of adding at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof and a step of adding a second viscosity reducing excipient.

The invention further provides a method for reducing the viscosity of a protein solution comprising a step of adding at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof and a step of adding a second excipient selected from the group consisting of valine, proline, leucine, isoleucine, phenylalanine, arginine, ornithine, carnitine, meglumine, camphorsulfonic acid and benzenesulfonic acid or salts or solvates thereof to the protein solution.

The invention further provides a method for reducing the viscosity of a protein solution, comprising a step of adding at least one first viscosity reducing excipient as mentioned above or salts or solvates thereof and a second viscosity reducing excipient as mentioned above or salts or solvates thereof.

The invention further provides a method for reducing the viscosity of a protein solution, comprising a step of adding at least one first viscosity reducing excipient selected from the group consisting of pyridoxine, folic acid, thiamine monophosphate and phenylalanine or salts or solvates thereof and a second viscosity reducing excipient selected from the group consisting of arginine, ornithine, carnitine, meglumine, camphorsulfonic acid and benzenesulfonic acid or salts or solvates thereof to the protein solution.

The invention further provides a method for reducing the viscosity of a protein solution, wherein the combination of a first and a second viscosity reducing excipient is selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

The invention further provides a method for reducing the viscosity of a protein solution as described above, whereas the protein in the protein solution has a molecular weight from 120 kDa to 250 kDa, preferably from 130 kDa to 180 kDa.

The invention further provides a method for reducing the viscosity of a protein solution as described above, whereas the protein concentration in the protein solution is at least 1 mg/ml, at least 50 mg/ml, preferably at least 75 mg/ml and more preferably at least 100 mg/ml. In another preferred embodiment, the protein concentration is between 90 mg/ml and 300 mg/ml, more preferably the protein concentration is between 100 and 200 mg/ml. The present invention is particularly useful for these high-concentration protein solutions.

The invention further provides a method for reducing the viscosity of a protein solution as described above, whereas the protein solution is further comprising a buffer at a concentration of 5 mM to 50 mM, preferably 10 mM to 50 mM. The buffer can be a suitable acetate- or phosphate salt and provide a pH of 5 to 7.2.

The invention further provides a method for reducing the viscosity of a protein solution as described above, whereas the protein solution is further comprising a sugar as stabilizer, preferably 50 to 100 mg/ml sucrose.

The invention further provides a method for reducing the viscosity of a protein solution as described above, whereas the protein solution is further comprising a surfactant, preferably 0.01 to 0.2 mg/ml, more preferably 0.05 mg/ml of polysorbate 80.

The invention further provides a method for reducing the viscosity of a protein solution as described above, whereas the resulting viscosity of the solution is between 1 mPas and 60 mPas, preferably between 1 mPas and 50 mPas, more preferably between 1 mPas and 30 mPas, most preferably between 1 mPas and 20 mPas. Preferably the viscosity is measured at 20° C., using a microfluidic viscometer. More preferably the viscosity is measured using a RheoSense mVROC microfluidic viscometer at 20° C. Most preferably the viscosity is measured using a RheoSense mVROC microfluidic viscometer at 20° C., using a 500 μl syringe, a shear rate of 3000 s-1 or 2000 s-1 and a volume of 200 μl.

The invention further provides a method for reducing the viscosity of a protein solution as described above, whereas viscosity is reduced by at least 5%, 10%, 15%, 20%, 25%, 30%, 35%, 40%, 45%, 50%, 55%, 60%, 65%, 70% or 75% compared to an identical composition not comprising the at least one first excipient or not comprising the at least one first and at least one second excipient.

The invention further provides a method for reducing the viscosity of a protein solution as described above, whereas the protein in the protein solution has a molecular weight from 120 kDa to 250 kDa at a concentration between 90 mg/ml to 300 mg/ml, the solution is further comprising an acetate buffer or phosphate buffer at a concentration between 10 mM to 50 mM, wherein the solution formulation has a pH between 5 and 7.2, and a viscosity between 1 mPas and 60 mPas when measured at 20° C., preferably using a microfluidic viscometer, more preferably using a RheoSense mVROC microfluidic viscometer at 20° C., most preferably using a RheoSense mVROC microfluidic viscometer at 20° C. with a 500 μl syringe, a shear rate of 3000 s-1 or 2000 s-1 and a volume of 200 μl.

The invention further provides a method for reducing the viscosity of a protein solution as described above, wherein a first and a second viscosity reducing excipient are present as mentioned above. Preferably, such embodiments of the invention have a protein concentration between 90 mg/ml to 300 mg/ml, more preferably between 100 mg/ml and 200 mg/ml and a concentration of the first and second viscosity reducing excipient between 50 and 200 mM each, more preferably between 50 and 100 mM each, most preferably 75 mM each. Preferably the protein is an antibody and has a molecular weight from 120 kDa to 250 kDa. Preferably the formulation has a pH between 5 and 7.2 and the viscosity is between 1 mPas and 60 mPas when measured at 20° C., preferably using a microfluidic viscometer.

Likewise, the invention is directed to methods for increasing the stability of a protein solution comprising a step of adding at least one viscosity reducing excipient selected from the group consisting of valine, leucine, ascorbic acid, cyanocobalamin and proline or salts or solvates thereof to the solution.

The invention further provides a method of preventing self-association of a protein in a solution by adding at least one first excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof to the solution or a combination of at least two viscosity reducing excipients as mentioned above.

In one aspect, combinations of first excipients are added in the methods of the invention. The combinations used in the methods of invention may be the same ones as defined for the compositions and formulations of the invention.

In one aspect, the methods of the invention further comprise a step of adding a second excipient selected from the group consisting of valine, proline, leucine, isoleucine, phenylalanine, arginine, ornithine, carnitine, meglumine, camphorsulfonic acid and benzenesulfonic acid to the solution. Herein, the same combinations of first and second excipients as defined for the compositions and formulations of the invention may be added.

In the methods according to the invention, the excipients may be added in any way known to the artisan to the protein solution. When more than one excipient is added, the excipient may be mixed together to form a viscosity-reducing solution which is then added to the protein solution. Likewise, the excipients may be added separately to the protein solution.

In the methods according to the invention, the protein may be a therapeutic protein. In a preferred embodiment, the protein is an antibody as defined above. In the methods according to the invention, the protein may be a plasma derived protein. In a further preferred embodiment, the protein is an IgG or hyper-IgG as defined above.

In a preferred embodiment of the invention the liquid composition is a pharmaceutical composition. The invention is also directed to a pharmaceutical composition as described above comprising a therapeutic protein for the treatment of disease.

In particular pharmaceutical compositions as described above comprising a therapeutic protein are suitable for the treatment of cancer, rheumatoid arthritis, morbus crohn, colitis ulcerose, ankylosing spondylitis, psoriasis-arthritis, psoriasis, hypercholesterolemia, mixed dyslipidemia, homozygous familial hypercholesterolemia, myocardial infarction, peripheral arterial disease or immune deficiency disorders.

The invention is also directed to methods of treatment, wherein the treatment comprises administration of a pharmaceutical composition as described above comprising a therapeutic protein.

In one aspect, the method of treatment is a method of treating cancer. That is, the compositions and formulations according to the invention are useful for the treatment of cancer, rheumatoid arthritis, morbus crohn, colitis ulcerose, ankylosing spondylitis, psoriasis-arthritis, psoriasis, hypercholesterolemia, mixed dyslipidemia, homozygous familial hypercholesterolemia, myocardial infarction, peripheral arterial disease or immune deficiency disorders.

At a protein concentration of 122 mg/ml as determined via absorption spectroscopy the protein viscosity has exceeded the limit of convenient injectability in the absence of excipients. The limit of convenient injectability is dependent on many factors, such as the length and inner diameter of the needle, the inner diameter of the syringe barrel. It is known, that drug products with a viscosity of up to 100 mPas can be injected to the patient. However, a viscosity of 60 mPas is preferred. Lower viscosities of below 30 mPas or below 20 mPas are even more preferred due to increased patient convenience.

Addition of valine, leucine, phenylalanine or proline reduced the viscosity of the formulation. At a higher concentration of 143 mg/ml the viscosity of the formulation in the absence of excipient is dramatically increased to values above 80 mPas. Addition of leucine, phenylalanine and proline reduced viscosity of the formulation.

In this experiment phenylalanine was found to be the most efficient viscosity reducing excipient, in particular for higher protein concentration.

At a protein concentration of 149 mg/ml addition of 150 mM pyridoxine, thiamine hydrochloride or thiamine monophosphate was found to reduce the viscosity of the formulation. Also, addition of 5 mM cyanocobalamin, 13 mM folic acid or 75 mM of thiamine pyrophosphate was found to reduce the viscosity of the formulation. Especially thiamine hydrochloride show a high viscosity reducing potential.

At an even higher protein concentration of 174 mg/ml a viscosity reducing effect of 150 mM pyridoxine, ascorbic acid, thiamine hydrochoride or thiamine phosphate was observed. Also, addition of 5 mM cyanocobalamin, 13 mM folic acid or 75 mM of thiamine pyrophosphate was found to reduce the viscosity of the formulation compared to a formulation without viscosity reducing excipients. Especially thiamine hydrochloride, thiamine monophosphate showed a high viscosity reducing potential. Thiamine pyrophosphate and thiamine hydrochloride, thiamine monophosphate were assessed at even higher protein concentrations of 152 mg/ml and 185 mg/ml. 75 mM thiamine pyrophosphate and 150 thiamine hydrochloride, thiamine monophosphate were found to have a strong viscosity reducing effect on the Infliximab solution.

An increase of the thermodynamic transition temperature characterizing heat induced protein unfolding (Tm) was observed upon the addition of 150 mM valine, leucine, ascorbic acid, or proline. Likewise addition of 5 mM cyanocobalamin resulted in an increase of Tm. Additionally, addition of 150 mM valine, leucine, ascorbic acid, and proline led to an increase of the aggregation onset temperature Tagg.

Using excipient combinations the thermodynamic unfolding temperature can likewise be increased. We observe an increase of Tm for combinations comprising of each 75 mM Cation/Anion when using ornithine/pyridoxine, ornithine/thiamine monophosphate, ornithine/thiamine pyrophosphate, arginine/pyridoxine, arginine/thiamine monophosphate, arginine/thiamine pyrophosphate, carnitine/pyridoxine, carnitine/thiamine monophosphate, phenylalanine/thiamine monophosphate, and, phenylalanine/thiamine pyrophosphate.

At a protein concentration of 192 mg/ml, as measured using absorption spectroscopy, a reduced viscosity for Evolocumab formulations upon addition of 150 mM leucine, isoleucine, phenylalanine, lysine, and guanidine hydrochloride was observed. When a higher protein concentration of 192 mg/ml was used, a reduced viscosity using 150 mM leucine, isoleucine, phenylalanine, proline, lysine, and guanidine hydrochloride as excipients was observed. Leucine, lysine and guanidine hydrochloride, showed the most pronounced viscosity reducing effect.

At a protein concentration of 180 mg/ml determined using a Bradford assay, viscosity of a Evolocumab formulation was reduced upon addition of 150 mM pyridoxine or thiamine hydrochloride. Likewise, addition of 5 mM cyanocobalamin, 25 mM quinine hydrochloride or 75 mM paracetamol reduced viscosity of the formulation.

At an even higher protein concentration of 196 mg/ml addition of 150 mM pyridoxine, thiamine hydrochloride or ascorbic acid reduced viscosity of the formulation. Also, the addition of 5 mM cyanocobalamin, 25 mM quinine hydrochloride or 75 mM Paracetamol reduced the viscosity of the formulation. In this data set thiamine hydrochloride was found to be the most efficient viscosity reducing excipient.

In a third data set viscosity reducing capacity of 75 mM thiamine pyrophosphate and 150 mM thiamine hydrochloride, thiamine monophosphate were compared. Both excipients reduced the viscosity of a Evolocumab formulation. 75 mM thiamine pyrophosphate is highly efficient when used for formulations with 179 mg/ml and 204 mg/ml Evolocumab. 150 mM thiamine monophosphate was only tested at a Evolocumab concentration of 180 mg/ml.

It has been found that combinations of two viscosity reducing excipients can synergistically reduce the viscosity of a protein solution. The percentual viscosity of an Infliximab formulation at 150 mg/ml, pH 7.2 was synergistically reduced upon addition of a combination of ornithine and folic acid and a combination of carnitine and folic acid.

The percentual viscosity of an Evolocumab formulation at 190 mg/ml, pH 5.0 was synergistically reduced upon addition of a combination of phenylalanine and camphorsulfonic acid, a combination of phenylalanine and benzenesulfonic acid, a combination of arginine and pyridoxine, a combination of meglumine and pyridoxine and a combination of meglumine and thiamine monophosphate.

Furthermore, it has been found that the excipients and excipient combinations as mentioned above are beneficial in the bioprocess. Experiments according to the present invention suggest that excipients and excipient combinations are suitable to reduce the backpressure on chromatography columns and allow for larger flow rates. This leads to less shear forces straining the proteins in the solution and therefore, aggregation will be reduced. Altogether a higher yield can be obtained. Beyond this, when the process can be run using higher flow rates, the process time will be reduced significantly.

In bioprocesses as meant here, the addition of these excipients, which are found to serve as viscosity-reducing additives, lead to an improved process economy, in that on the one hand the yield of intact protein can be improved, and on the other hand the duration of the process can be reduced.

In the present invention the foundation of the experiments conducted is laid by Amicon® centrifugal filtration studies. These experiments resemble any process step, where a solution is passed through a filter membrane by centrifugal force. The resistance to the centrifugal force is dependent on the properties of the filter, which is assumed to be constant within the context of this experiments, and the viscosity of the solution. Excipients and excipient combinations that provide the most favorable solutions are selected for more complex experiments using stirred cells.

In experiments using Amicon® stirred cells nitrogen gas is used to apply pressure to the solution that is being pressed through a filter. The resistance of the pressure is dependent on the properties of the filter, which is assumed to be constant within the context of this experiments, and the viscosity of the solution. The excipient combination that gives most favorable results is used in an experiment using a laboratory scale tangential flow filtration (TFF) system.

These experiments highlight the beneficial effects of viscosity reducing agents during dead-end filtration approaches. Additionally, it becomes clear that in technical approaches, where a solution is passed through a filter or medium, like a gel bed, by a force applied by back-end pressure, e.g. during chromatographic purifications, the disclosed viscosity reducing excipients have beneficial effects. While said filtration steps are mainly used in the downstream process, viscosity reducing excipients can also be beneficial in the upstream process. When protein concentrations elevate to levels where they cause viscosity, with the described negative effects of pressure limitations and shear forces when the solution is passed through a tubing or a filter to remove cellular material and debris the presented invention will obviously have beneficial effects. To measure process efficiency in tangential flow filtration, where in contrast to previously used method the majority of the field flow travels tangentially across the surface of the filter, rather than passing through the filter, a laboratory scale TFF system was used. While the filtration principle is different than in the methods described previously, also here the filtration efficiency depends on the resistance of the membrane, which also here remains constant, and the solution viscosity, which is modified by the invention. Filtration methods are typical unit operation used to exchange a formulation buffer or to bring the concentration of a biomolecule to the desired level. The stirred cells used herein are representation of dead-end filters, where a feed is passed through a filtering material that withholds larger molecules on top of the material releasing the filtrate on the other end of the device.

A frequent method to exchange buffers and to concentrate proteins is tangential flow filtration, where in contrast to previously used methods the majority of the field flow travels tangentially across the surface of the filter, rather than passing through the filter. Like when stirred cells are used in tangential flow filtration the large molecules are separated from smaller molecules by passing said smaller molecules through a suitable filter material. In contrast to stirred cells, which represent one form of dead end filtration, in tangential flow filtration the flow geometry of the feed is different to avoid the formation of a filter cake and allowing for a continuous process. When stirred cells are used the formation of a filter cake is likewise prevented by the use of a stirring device. Therefore, the stirred cells closely resemble a tangential flow filtration device in spite of the differences in filter geometry. The efficiency of both methods is critically depending on the membrane resistance. Also, a high viscosity is known to reduce the flux rate that can be used and therefore increasing processing time resulting in higher production costs. It is therefore expected that a reduced viscosity allows for a more efficient filtration process while shear forces remain low yielding to a higher protein concentration in the filtrate. This is highlighted by the work of Hung et al. who state: "During production of concentrated monoclonal antibody formulations by tangential flow ultrafiltration (TFF), high viscosities and aggregation often cause extensive membrane fouling, flux decay and low product yields" (Journal of Membrane Science Volume 508, 15 Jun. 2016, Pages 113-126)

Experiments have shown that viscosity reducing excipients selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof are suitable to improve bioprocess economics as described before. Furthermore, viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or salts or solvates thereof in combination with a second viscosity reducing excipient selected from the group consisting of valine, proline, leucine, isoleucine, phenylalanine, arginine, ornithine, carnitine, meglumine, camphorsulfonic acid and benzenesulfonic acid improve bioprocess economics. Especially combinations in various ratios depending on the protein solutions improve bioprocess economics as described.

Therefore, another aspect of the present invention is to provide a method for reducing the viscosity of a protein solution in a bioprocess, comprising a protein in a concentration in the range of at least 90 mg/ml up to 300 mg/ml, comprising the step of combining the protein solution with first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol. In another aspect, the protein solution is combined with a first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method for reducing the viscosity of a protein solution as described above in a bioprocess.

According to the present invention all parameters mentioned above; e.g. combinations of the excipients, concentrations of the excipients, concentrations the protein, ratios of the excipients, further elements of the composition such as buffers or stabilizers, pH values, viscosity reductions, specifications of the protein, molecular weight of the protein also apply to the use in bioprocess.

Preferably the at least one first viscosity reducing excipient is selected from the group consisting of pyridoxine, folic acid, thiamine monophosphate and phenylalanine and at least one second viscosity reducing excipient is selected from the group consisting of arginine, ornithine, carnitine, meglumine, camphorsulfonic acid and benzenesulfonic acid.

Preferably a combination is used comprising a first and a second viscosity reducing excipient selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

Preferably the first viscosity reducing excipients is thiamine, thiamine monophosphate, thiamine pyrophosphate or pyridoxine, more preferably thiamine and thiamine pyrophosphate. Preferably a concentration of 75-500 mM, more preferably 75-150 mM, most preferably 75 mM or 150 mM is used.

Preferably the second viscosity reducing excipients is arginine or ornithine. Preferred combinations are thiamine and arginine as well as thiamine and ornithine. Preferably the concentration of each excipient is 75-500 mM, more preferably 75-150 mM, most preferably 75 mM or 150 mM.

When a first viscosity reducing excipient is used in combination with a second viscosity reducing excipient, the ratio is in the range of 1:3 to 3:1, more preferred 1:2 to 2:1, most preferred 1:1.

Depending on the protein solution and the bioprocess carried out, different buffer systems may be used as buffers. Acetates, like ammonium acetate, or sodium acetate, carbonates like ammonium bicarbonate or sodium bicarbonate, or phosphates, like sodium phosphate or Tris-phosphate may be used here, depending on the conditions during the bioprocess.

Another aspect of the present invention is to provide a method for reducing the viscosity of a protein solution in a bioprocess as mentioned above, wherein the permeate flux of the protein solution in a filtration step is increased compared to an identical protein solution not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method in a bioprocess as mentioned above, wherein the permeate flux of the protein solution in a filtration step is increased compared to an protein solution composition not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is to provide a method for reducing the viscosity of a protein solution in a bioprocess as mentioned above, wherein the permeate flux of the protein solution in a filtration step is increased compared to an identical protein solution not comprising at least one first viscosity reducing excipient selected from the group consisting of pyridoxine, folic acid, thiamine monophosphate and phenylalanine and at least one second viscosity reducing excipient selected from the group consisting of arginine, ornithine, carnitine, meglumine, camphorsulfonic acid and benzenesulfonic acid.

Another aspect of the present invention is to provide a method for reducing the viscosity of a protein solution in a bioprocess as mentioned above, wherein the permeate flux of the protein solution in a filtration step is increased compared to an identical protein solution not comprising a combination of a first and a second viscosity reducing excipient selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

Increase of permeate flux means a percentage increase of at least 2%, preferably at least 5%, more preferably at least 10%, most preferred 10% to 100%.

Another aspect of the present invention is to provide a method for reducing the viscosity of a protein solution in a bioprocess as mentioned above, wherein the protein recovery after buffer exchange and volume reduction in filters is increased compared to an identical protein solution not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method in a bioprocess as mentioned above, wherein the protein recovery after buffer exchange and volume reduction in filters is increased compared to an identical protein solution not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method in a bioprocess as mentioned above, wherein the protein recovery after buffer exchange and volume reduction in filters is increased compared to an identical protein solution not comprising at least one first viscosity reducing excipient selected from the group consisting of pyridoxine, folic acid, thiamine monophosphate and phenylalanine and at least one second viscosity reducing excipient selected from the group consisting of arginine, ornithine, carnitine, meglumine, camphorsulfonic acid and benzenesulfonic acid.

Another aspect of the present invention is the use of the method in a bioprocess as mentioned above, wherein the protein recovery after buffer exchange and volume reduction in filters is increased compared to an identical protein solution not comprising a combination of a first and a second viscosity reducing excipient selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

Increase of protein recovery after buffer exchange and volume reduction in filters means a percentage increase of protein recovery of at least 1%, preferably at least 2%, more preferably at least 5%, most preferred 5% to 20%.

Another aspect of the present invention is to provide a method for reducing the viscosity of a protein solution in a bioprocess as mentioned above, wherein the process time for a filtration step, preferably a filtration step wherein the protein is concentrated, is reduced compared to an identical protein solution not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method in a bioprocess as mentioned above, wherein the process time for a filtration step, preferably a filtration step wherein the protein is concentrated, is reduced compared to an identical protein solution not comprising camphorsulfonic acid or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol or compared to an identical protein solution not comprising at least one first viscosity reducing excipient selected from the group consisting of cyanocobalamin, pyridoxine, ascorbic acid, folic acid, thiamine, thiamine monophosphate, thiamine pyrophosphate, guanidine hydrochloride, quinine hydrochloride and paracetamol and a second viscosity reducing excipient selected from the group consisting of valine, proline, leucine, isoleucine, phenylalanine, arginine, ornithine, carnitine, meglumine, camphorsulfonic acid and benzenesulfonic acid.

Another aspect of the present invention is the use of the method in a bioprocess as mentioned above, wherein the process time for a filtration step, preferably a filtration step wherein the protein is concentrated, is reduced compared to an identical protein solution not comprising at least one first viscosity reducing excipient selected from the group consisting of pyridoxine, folic acid, thiamine monophosphate and phenylalanine and at least one second viscosity reducing excipient selected from the group consisting of arginine, ornithine, carnitine, meglumine, camphorsulfonic acid and benzenesulfonic acid.

Another aspect of the present invention is the use of the method in a bioprocess as mentioned above, wherein the process time for a filtration step, preferably a filtration step wherein the protein is concentrated, is reduced compared to an identical protein solution not comprising a combination of a first and a second viscosity reducing excipient selected from the list consisting of pyridoxine and arginine, folic acid and ornithine, folic acid and carnithine, pyridoxine and meglumine, thiamine monophosphate and meglumine, pyridoxine and thiamine monophosphate, phenylalanine and camphorsulfonic acid and phenylalanine and benzenesulfonic acid.

Reduction of process time for a filtration step means a percentage reduction of at least 5%, preferably at least 10%, more preferably at least 25%, most preferred 25% to 100%.

In a particular embodiment of the invention, the filtration step is a tangential flow filtration (TFF).

The term "bioprocess" refers to therapeutic cell manufacturing processes, which can be separated into upstream processes and downstream processes. The upstream process is defined as the entire process prior to separating protein from cellular compounds. The upstream process comprises early cell isolation and cultivation, to cell banking and culture expansion of the cells until final harvest. The downstream part of a bioprocess refers to the part where the target protein is purified from the feed of the upstream and is processed to meet purity and quality requirements. Some type of cells need to be disrupted when entering the downstream process. Yet other cells may secrete the target protein into the media and need to be removed via filtration. Further downstream processing is usually divided into the main sections: a purification section and a polishing section. A bioprocess can be a batch process or a semi-continuous or a continuous process.

The term "permeate flux" refers to the volume passing through a defined filter within a certain period of time, typically on the order of minutes.

The term "filtration step" refers to a process step where a liquid is passed through a material with a defined pore size allowing for the separation of materials based on their size. For some filters the pore size is defined in nanometers. Yet for other filters, the pore size is not directly defined, but the weight of a molecule to be withheld is given. Filtering materials can be placed in a way that they block the cross-section of the filtration device (dead-end filtration). Yet filtering materials can be placed in a way that the solution to be filtered is tangentially flowing across the surface of said material, e.g. tangential flow filtration. The filtering material can be a membrane, a glass filter, a metallic filter or a resin. The resin can be held in a chromatography column. The resin can be a cationic or anion exchange resin, an affinity resin, like a Protein A or glutathione resin, or a hydrophobic or hydrophilic resin.

The term "protein recovery" after buffer exchange and volume reduction refers to the fraction of protein to be retrieved after a process step.

The term "tangential flow filtration" or "TFF" refers to a method of filtration where a solution passes over a defined filter tangentially. Substances smaller than the filter pores are forced out of the solution through the filter by the pressure resulting from solution flow rate, viscosity, temperature and other factors.

EXAMPLES

1. Viscosity Measurements

1.1 Viscosity Reducing Effect of Valine, Leucine, Phenylalanine, Proline, Ascorbic Acid, Pyridoxine, Cyanocobalamin, Thiamine Hydrochloride, Folic Acid, Thiamine Pyrophosphate and Thiamine Monophosphate on Infliximab Formulated in Phosphate Buffer at pH 7.2

Buffer Preparation 5 mM phosphate buffer was prepared by appropriately mixing sodium dihydrogenphosphate and di-sodium hydrogenphosphate to yield a pH of 7.2 and dissolving the mixture in ultrapure water. The ratio was determined using the Henderson-Hasselbalch equation. pH was adjusted using HCl and NaOH where necessary.

50 mg/ml sucrose and 0.05 mg/ml polysorbate 80 were added as stabilizers.

Sample Preparation

Individual excipient solutions of 150 mM valine, leucine, phenylalanine, ascorbic acid, pyridoxine, proline and thiamine monophosphate were prepared in phosphate buffer pH 7.2. In the same buffer, a 5 mM solution of cyanocobalamin was prepared. Folic acid was prepared in a 13 mM concentration in phosphate puffer pH 7.2. Thiamine pyrophosphate was prepared in a 75 mM concentration in phosphate puffer pH 7.2. The pH was adjusted using HCl or NaOH where necessary.

A concentrated Infliximab solution containing the desired excipients was prepared using centrifugal filters (Amicon, 30 kDa MWCO) to exchange the original buffer with a buffer containing the respective excipient and to reduce the volume of the solution. The protein was subsequently diluted to 122 mg/ml and 143 mg/ml, respectively.

Protein Concentration Measurements

Protein Concentration was determined using absorption spectroscopy applying Lambert-Beer's law. When excipients themselves had a strong absorbance at 280 nm, a Bradford assay was used.

Concentrated protein solutions were diluted so that their expected concentration would lie between 0.3 and 1.0 mg/mL in the measurement.

For absorption spectroscopy, the absorbance at 280 nm was measured using a BioSpectrometer® kinetic (Eppendorf, Hamburg, Germany) with a protein extinction coefficient of $A_{0.1\%}$, 280 nm=1.428.

Some excipients have themselves a strong absorption at 280 nm, which makes it necessary to use a Bradford assay for concentration determination.

For the Bradford assay, a kit as well as Bovine Gamma Globulin Standard from Thermo Scientific™ (Thermo Fisher, Waltham, Massachusetts, USA) were used. Absorption was measured at 595 nm using a Multiskan™ Wellplatereader (Thermo Fisher, Waltham, Massachusetts, USA). Protein concentrations were determined by linear regression of a standard curve from 125 to 1500 μg/ml.

Viscosity Measurements

The mVROC™ Technology (Rheo Sense, San Ramon, California, USA) was used for viscosity measurements.

Measurements were performed at 20° C. using a 500 μl syringe and a shear rate of 3000 s-1. A volume of 200 μl was used. All samples were measured as triplicates.

Results of viscosity measurements regarding these experiments can be seen in FIG. 1, FIG. 2 and FIG. 3.

1.2 Viscosity Reducing Effect of Leucine, Isoleucine, Phenylalanine, Proline, Lysine, Guanidine Hydrochloride, Ascorbic Acid, Pyridoxine, Cyanocobalamin, Quinine Hydrochloride, Thiamine Hydrochloride, Paracetamol, Thiamine Pyrophosphate and Thiamine Monophosphate on Evolocumab Formulated in Acetate Buffer pH 5.0

Buffer Preparation 20 mM Acetate buffer was prepared by mixing 1.2 mg/ml glacial acetic acid with ultrapure water. pH was adjusted to 5.0 using HCl and NaOH if necessary. 0.1 mg/ml Polysorbate 80 was added as stabilizer Sample Preparation Excipient solutions of 150 mM leucine, isoleucine, phenylalanine, ascorbic acid, pyridoxine, proline, lysine, guanidine hydrochloride, thiamine hydrochloride, thiamine monophosphate were prepared in acetate buffer pH 5.0, respectively. Similarly, 25 mM quinine hydrochloride and 5 mM cyanocobalamin were prepared, respectively. Paracetamol and thiamine pyrophosphate were prepared with a concentration of 75 mM. The pH was adjusted using HCl or NaOH, if necessary. A concentrated Evolocumab solution containing the desired excipients was prepared using centrifugal filters (Amicon, 30 kDa MWCO) to exchange the original buffer with a buffer containing the relevant excipients and to reduce the volume of the solution. The protein was subsequently diluted to 172 mg/ml and 192 mg/ml respectively for experiments regarding leucine, isoleucine, phenylalanine, proline, lysine and guanidine hydrochlorid, 180 and 196 mg/ml for experiments regarding ascorbic acid, pyridoxine, cyanocobalamin, quinine hydrochloride, thiamine hydrochloride and paracetamol, and 179 and 204 mg/ml for experiments regarding thiamine pyrophosphate and thiamine monophosphate.

Protein Concentration Measurements

Protein Concentration was determined using absorption spectroscopy applying Lambert-Beer's-Law. When excipients themselves have a strong absorbance at 280 nm a Bradford-Assay was used.

Concentrated protein solutions were diluted so that their expected concentration would lie between 0.3 and 1.0 mg/mL in the measurement.

For absorption spectroscopy the absorbance at 280 nm was measured at 280 nm using a BioSpectrometer® kinetic (Eppendorf, Hamburg, Germany) with a protein extinction coefficient of $A_{0.1\%,\ 280\ nm}$=1.428.

For Bradford-Assay a kit as well as a Bovine Gamma Globulin Standard from Thermo Scientific™ (Thermo Fisher, Waltham, Massachusetts, USA) was used. Absorption was measured at 595 nm using a Multiskan™ Wellplatereader (Thermo Fisher, Waltham, Massachusetts, USA). Protein Concentrations were determined by linear regression of a standard curve from 125 to 1500 μg/mL.

Viscosity Measurements

The mVROC™ Technology (Rheo Sense, San Ramon, California USA) was used for viscosity measurements.

Measurements were performed at 20° C. using a 500 μl syringe and a shear rate of 3000 $s^{-1}$ for protein solutions from 160-179 mg/ml and of 2000 $s^{-1}$ for protein solutions from 180-210 mg/ml. A volume of 200 μl was used. All samples were measured as triplicates.

Results of viscosity measurements regarding these experiments can be seen in FIG. 4, FIG. 5 and FIG. 6.

1.3 Viscosity Reducing Effect of Combinations of Thiamine Hydrochloride, Pyridoxine, Folic Acid, Phenylalanine, Thiamine Monophosphate and Thiamine Pyrophosphate on Infliximab Formulated in Phosphate Buffer, pH 72.

Buffer Preparation 5 mM Phosphate buffer was prepared by appropriately mixing sodium dihydrogenphosphate and di-sodium hydrogenphosphate to yield a pH of 7.2 and dissolving the said mixture in ultrapure water. The said ratio was determined using the Henderson-Hasselbalch equation. pH was adjusted using HCl and NaOH if necessary.

50 mg/ml Sucrose and 0.05 mg/ml Polysorbate 80 were added as stabilizers.

Sample Preparation

Excipient solutions of 75 mM thiamine hydrochloride or 75 mM phenylalanine dissolved in phosphate buffer, pH 7.2 were supplemented with 75 mM pyridoxine, 12 mM folic acid, 75 mM thiamine monophosphate or thiamine pyrophosphate.

A concentrated Infliximab solution containing the desired excipients was prepared using centrifugal filters (Amicon, 30 kDa MWCO) to exchange the original buffer with a buffer containing the relevant excipients and to reduce the volume of the solution. The protein was subsequently diluted to 122 mg/ml and 154 mg/ml respectively.

Protein Concentration Measurements

Protein Concentration was determined using a Bradford-Assay.

Therefore a kit from Thermo Scientific™ (Thermo Fisher, Waltham, Massachusetts, USA) as well as a Infliximab-Standard prepared by using absorption spectroscopy applying Lambert-Beer's-Law were used. Absorption was measured at 595 nm using a Multiskan™ Wellplatereader (Thermo Fisher, Waltham, Massachusetts, USA). Protein Concentrations were determined by an appropriate polynomial regression of a standard curve from 125 to 1500 μg/mL.

Viscosity Measurements

Viscosity Measurements were performed according to the method described under 1.1.

Results of viscosity measurements regarding these experiments can be seen in FIG. 7.

1.4 Viscosity Reducing Effect of Combinations of a First Set Consisting of L-Ornithine, L-Arginine, L-Carnitine, Camphorsulfonic Acid and Benzenesulfonic Acid and a Second Set Consisting of Thiamine Hydrochloride, Phenylalanine, Pyridoxine, Folic Acid, Thiamine Monophosphate and Thiamine Pyrophosphate on Infliximab Formulated in Phosphate Buffer, pH 72.

Buffer Preparation

Buffer Preparation was performed according to the method described under 1.3.

Sample Preparation

Excipient solutions of 75 mM L-ornithine monohydrochloride, L-arginine, L-carnitine hydrochloride or phenylalanine dissolved in phosphate buffer, pH 7.2 were supplemented with 75 mM pyridoxine, 12 mM folic acid, 75 mM thiamine monophosphate or 75 mM thiamine pyrophosphate. 75 mM thiamine hydrochloride or phenylalanine were supplemented with 75 mM camphorsulfonic acid or benzenesulfonic acid.

A concentrated Infliximab solution containing the desired excipients was prepared as described under 1.3.

Protein Concentration Measurements

Protein Concentration Measurements were performed according to the method described under 1.3.

Viscosity Measurements

Viscosity Measurements were performed according to the method described under 1.1.

Results of viscosity measurements regarding these experiments can be seen in FIG. 8.

1.5 Viscosity Reducing Effect of Sodium Chloride, Arginine and Combinations of a First Set Consisting of L-Ornithine, L-Arginine, L-Carnitine, Meglumine, Camphorsulfonic Acid and Benzenesulfonic Acid and a Second Set Consisting of Thiamine Hydrochloride, Pyridoxine, Thiamine Monophosphate and Thiamine Pyrophosphate on Evolocumab Formulated in Acetate Buffer, pH 5.0.

Buffer Preparation 20 mM Acetate buffer was prepared by mixing 1.2 mg/ml glacial acetic acid with ultrapure water. pH was adjusted to 5.0 using HCl and NaOH if necessary.

0.1 mg/ml Polysorbate 80 was added as stabilizer

Sample Preparation

Excipient solutions of 75 mM L-ornithine monohydrochloride, L-arginine, L-carnitine hydrochloride or meglumine dissolved in acetate buffer, pH 5.0 were supplemented with 75 mM pyridoxine, 75 mM thiamine monophosphate or 75 mM thiamine pyrophosphate. 75 mM thiamine hydrochloride were supplemented with 75 mM pyridoxine, camphorsulfonic acid or benzenesulfonic acid.

A concentrated Evolocumab solution containing the desired excipients was prepared using centrifugal filters (Amicon, 30 kDa MWCO) to exchange the original buffer with a buffer containing the relevant excipients and to reduce the volume of the solution. The protein was subsequently diluted to 163 mg/ml and 180 mg/ml, respectively.

Protein Concentration Measurements

Protein Concentration was determined using a Bradford-Assay Therefore a kit from Thermo Scientific™ (Thermo Fisher, Waltham, Massachusetts, USA) as well as a Evolocumab-Standard prepared by using absorption spectroscopy applying Lambert-Beer's-Law were used. Absorption was measured at 595 nm using a Multiskan™ Wellplatereader (Thermo Fisher, Waltham, Massachusetts, USA). Protein Concentrations were determined by an appropriate polynomial regression of a standard curve from 125 to 1500 µg/mL.

Viscosity Measurements

Viscosity Measurements were performed according to the method described under 1.2.

Results of viscosity measurements regarding these experiments can be seen in FIG. 9.

1.6 Synergies in Viscosity Reduction for a Combination of Arginine/Pyridoxine, Ornithine/Folic Acid, Carnithine/Folic Acid, Meglumine/Pyridoxine, Meglumine/Thiamine Monophosphate, Pyridoxine/Thiamine Monophosphate, Phenylalanine/Camphorsulfonic Acid and Phenylalanine/Benzenesulfonic Acid Samples of Infliximab at 150 mg/mL containing 75 mM L-ornithine monohydrochloride, L-carnitine hydrochloride, pyridoxine or thiamine monophosphate were prepared and analyzed as described in 1.1.

Samples of Evolocumab at 190 mg/mL containing 75 mM meglumine, camphorsulfonic acid, benzenesulfonic acid, pyridoxine or thiamine monophosphate were prepared and analyzed as described in 1.2.

For these data and data obtained in 1.1 to 1.5 the percentual reduction compared to a respective control sample not containing investigated viscosity reducing excipients (viscosity of control) was calculated. Using these percentual viscosity reductions an expected viscosity reduction could be calculated if one would combine those.

Expected values can not be calculated based on absolute values, since two combined excipients which reduce the viscosity by 50% each would result in a viscosity of 0 mPas. From a scientific point this is not feasible, especially in case the excipients reduce the viscosity by more than 50% resulting in negative viscosity values. Hence, the expected viscosity reduction of both excipients was determined based on a consecutive calculation:

Expected vicosity=Viscosity of control*(100%−viscosity reduction [%] 1$^{st}$ excipient)*(100%−viscosity reduction [%] 2$^{nd}$ excipient)

Example calculation for a combination of two excipients reducing the viscosity by (i) 50% each and (ii) 75% each in a solution with a viscosity of 100 mPas:

(i) Expected viscosity=100 mPas*(100%−50%)*(100%−50%)=25 mPas (i) Expected viscosity=100 mPas*(100%−75%)*(100%−75%)=6.25 mPas If for a combination of two excipients a lower viscosity, i.e. higher viscosity reduction is observed compared to the expected one, the combination is found to be synergistic.

FIG. 21 shows a synergistic viscosity reduction for the combinations ornithine/folic acid, carnitine/folic acid and pyridoxine/thiamine monophosphate. FIG. 22 shows a synergistic viscosity reduction for the combinations phenylalanine/camphorsulfonic acid, phenylalanine/benzenezesulfonic acid and arginine/pyridoxine. FIG. 23 shows a synergistic viscosity reduction for the combinations meglumine/pyridoxine and meglumine/thiamine monophosphate.

2. Thermal Stability Measurements 2.1 Thermal Stability of Infliximab Formulated in Phosphate Buffer pH 7.2 Containing Valine, Leucine, Ascorbic Acid, Cyanocobalamin and Proline as Single Excipients Buffers and samples were prepared as described under 1.1.

Thermal Stability Measurements

The nano-DSF Technology of a Prometheus system (NanoTemper Technologies GmbH, Munich, Germany) was used to determine melting points and aggregation points.

Fluorescence was measured at 330 and 350 nm as well as the backscattering intensity over a temperature range from 20 to 95° C. with an incline of 1° C./min.

Results of thermal stability measurements regarding these experiments can be seen in FIG. 10.

2.2 Thermal Stability of Infliximab Formulated in Phosphate Buffer pH 72 Containing Combinations of a First Set Consisting of L-Ornithine, L-Arginine, L-Carnitine, Phenylalanine and Benzenesulfonic Acid and a Second Set Consisting of Pyridoxine, Thiamine Monophosphate and Thiamine Pyrophosphate.

Buffers and samples were prepared as described under 1.4 and 1.5.

Thermal stability measurements were performed as described under 2.1.

Results of thermal stability measurements regarding these experiments can be seen in FIG. 11.

3. Storage Stability Measurements 3.1 Storage Conditions

The use of excipient combinations is beneficial to aid in managing the stability of a pharmaceutical formulation. To evaluate stability of said formulation, samples are stored at standardized conditions in terms of temperature and relative humidity. Typically assessed temperatures include 4° C., 20° C., 25° C., and 40° C. The relative moisture is typically 40%, 60% or 75%. Stability of protein formulations can be assessed using different criteria. Methods to measure said criteria need to be optimized and validated for the specific protein studied, a task that is obvious to a person skilled in the art.

We prepare pharmaceutical formulations of proteins at high concentrations >70 mg/ml and store them at 25° C. with a relative humidity of 60%. During the following 24 weeks samples are on 6 time points removed from storage and analyzed with respect to the following parameters: Fragmentation, aggregation/monomer content, content, conformational stability, particle content, and pH.

3.2 Protein Fragmentation Measurement

Fragmentation can be measured using an HPLC system with an appropriate size exclusion column that is sensitive to substances smaller than the antibody in question. Molecules are separated based on their size and the elution time of fragments shall be higher than the elution time of the intact protein. Fragments and protein are typically detected by absorption at 214 nm. Another method to detect fragmentation is denaturing gel electrophoresis, typically performed using a polyacrylamide gel containing sodium dodecyl sulphate (SDS-PAGE). SDS solubilizes proteins and their fragments masking potential charges and thereby allows for the separation of molecules by size within the gel matrix.

3.3 Protein Aggregation Measurement

Aggregation or monomer content can be measured using HPLC-SEC using a column suitable to determine the molecular weight of the target protein. When absorption at 214 nm is used, the numerical integral of the target protein peak can be used to determine the protein content of the sample. The protein content of a sample after incubation divided by a reference sample yields to the monomer content. In contrast to the HPLC method to determine fragmentation, the column used herein is suitable to detect molecular species that are larger than the target protein.

3.4 Protein Content Measurement

Protein content can be measured by the HPLC method described in the previous paragraph or alternatively using absorption spectroscopy applying the Lambert-Beer Equation. Additionally, a Bradford Assay may be used.

To probe for conformational stability a thermal shift assay using fluorescence spectroscopy can be employed. By measuring the heat denaturation mid-point Tm changes in the protein conformation can be discovered, since changes in Tm would report on changes in the structure of the measured protein.

3.5 Particle Analytical Method

Particles can be visualized by light obscuration methods e.g. turbidity measurements, flow Imaging techniques, and dynamic light scattering dependent on their respective size.

pH can be monitored by using a pH-electrode.

Generally, deviations of <10% of each parameter can be accepted. However, particle analytical method, in particular those focused on single particle counting, inherently have a comparatively high error of up to 30% due to the use of Possoinian statistics.

4. Benefits for Centrifugal Filter Units

Buffer Preparation

A 10 mM citrate buffer was prepared using citric acid monohydrate and dissolving it in ultrapure water. pH was adjusted using HCl and NaOH to 5.5 if necessary. 0.25 mg/mL Polysorbate 80 was added as stabilizer. Excipient solutions of Phenylalanine (Phe), Ornithine (OM), Arginine (Arg) Thiamine HCl, Thiamine monophosphate, and Thiamine pyrophosphate were prepared in citrate buffer, pH 5.5 with a concentration of 150 mM. Combinations containing two of these excipients were prepared with a concentration of 75 mM for each or 150 mM for each.

Sample Preparation

A Cetuximab solution containing approximately 14.7 mg/ml was used as starting material. Thereof, a sufficient volume was calculated to achieve a final concentration of more than 120 mg/ml in 500 μL sample assuming up to 20% sample loss.

Protein Concentration Measurements

Protein concentration was determined using absorption spectroscopy applying Lambert-Beer's-Law. When excipients themselves have a strong absorbance at 280 nm a Bradford-Assay was used.

Concentrated protein solutions were diluted so that their expected concentration would lie between 0.3 and 1.0 mg/mL in the measurement.

For absorption spectroscopy the absorbance at 280 nm was measured at 280 nm using a BioSpectrometer® kinetic (Eppendorf, Hamburg, Germany) with a protein extinction coefficient of A0.1%, 280 nm=1.4.

For excipients that absorbed light at 280 nm protein concentration was determined using a Bradford-Assay. Therefore, a kit from Thermo Scientific™ (Thermo Fisher, Waltham, Massachusetts, USA) as well as a Cetuximab-Standard prepared by using absorption spectroscopy applying Lambert-Beer's-Law were used. Absorption was measured at 595 nm using a Multiskan™ Wellplatereader (Thermo Fisher, Waltham, Massachusetts, USA). Protein Concentrations were determined by an appropriate polynomial regression of a standard curve from 125 to 1500 μg/mL.

Volume Measurement

Permeate volume was measured using a volumetric flask of an appropriate size.

For Amicon® centrifugal filter units the permeate was transferred to the volumetric flask after centrifugation. For Amicon® stirred cell experiments, the permeate was directly collected in a such one.

Volume of concentrated protein solutions were measured using a Multipette® E3X (Eppendorf, Hamburg, Germany) and Combitips Advanced® of an appropriate size.

Buffer Exchange and Volume Reduction

An Amicon® centrifugal filter with a 30 kDa MWCO was used to exchange the original buffer with a buffer containing the relevant excipients and to reduce the volume of the solution. Five diavolumes were used to exchange the original buffer with a buffer containing the relevant excipients.

To measure permeate flux, Amicon® centrifugal filters were centrifuged at 2000×g for 15 minutes and volume measured as described above (repeated four times and average calculated).

To achieve the final concentration, Amicon® centrifugal filters were centrifuged in small timesteps and cumulated duration denoted upon reaching the 500 μL mark.

FIG. 12 to FIG. 16 below highlight the process improvement indicated by an increased permeate flux.

5. Benefits for Stirred Cells

Excipients and combinations that had a positive effect in processing with Amicon® centrifugal filters were used in Amicon® stirred Cell filtration. While Amicon® spin column concentrators are driven by centrifugal force, stirred cells are operated by back pressure that is applied to the solution in form of nitrogen or airflow. This model system is frequently used to test processability of a solution and is a more closer model system compared to the previously used Amicon® centrifugal filters.

Buffer were prepared according to example 4.

Sample Preparation

The volume of antibody stock solution was calculated to yield at least 10 mL of a solution comprising 25 mg/mL cetuximab assuming a loss of up to 20%.

Protein concentration measurements and volume measurements were performed according to example 4.

Buffer Exchange and Volume Reduction

For stirred cell setup a model containing up to 50 mL was equipped with a Ultrafiltration disc filter with a NMWL of 30 kDa and an active membrane area of 13.4 $cm^2$. The respective volume of cetuximab stock solution was filled in the stirred cell and respective buffer added to the 50 mL mark. Five diavolumes were used to exchange the original buffer with a buffer containing the relevant excipient or combination.

To measure permeate flux, a pressure of 4 bar was applied on the Amicon® stirred cell at a mixing speed of 200 rpm (using magnetic stirrer plate) for 30 minutes (four times). For final concentration time, the cell was filled again to 50 mL mark with the respective buffer and 4 bar pressure applied at 200 rpm stirrer speed. Upon reaching the 10 mL mark, duration was denoted, process stopped and volume as well as concentration of the resulting antibody solution measured as described above.

As described in example 4, the effect on mean permeate flux of the formulation is assessed first. Results are depicted in FIG. 17 to FIG. 19.

6. Benefits for Processing with TFF

Based on previous experiments using Amicon® Filters and Stirred Cell, one excipient combination was selected to evaluate filtration benefits in a tangential flow filtration system. This system represents the closest model to a large scale bioprocessing step. As the excipient combination used herein showed a beneficial effect on the process mimicked by the two previous steps it is assumed that other excipients with positive effects on process efficiency and recovery prior would have a similar effect in this setting as well.

Buffer were prepared according to example 4.

Sample Preparation

The volume of antibody stock solution was calculated to yield at least 30 mL of a solution comprising 80 mg/mL Cetuximab assuming a loss of up to 20%.

Protein concentration measurements and volume measurements were performed according to example 4.

Buffer Exchange and Volume Reduction

An ÄKTA flux S cross flow filtration system (GE Healthcare, Marlborough, Massachusetts USA) equipped with a Pellicon® XL cassette, Biomax® 30 kDa, device size: 50 $cm^2$ and a 500 ml reservoir was used to assess process benefits. An above specified amount of a cetuximab solution was given into the reservoir and filled to the 450 ml mark. Using a transfer pump four further diavolumes were added stepwise while the sample was circulated in the system. For sample concentration, feed flow rate was adjusted to 30 ml/min and stirrer speed to 60 rpm. Process was either stopped by minimal tank level of 20 g or by reaching a feed pump pressure of 4 bar. Concentrated antibody solution was recovered using in-line outlets of the system.

In FIG. 20 the tank level and the pressure is plotted vs. the process time. A formulation without excipient vs. a formulation where 75 mM Ornithine and 75 mM ThiamineHCl are used to manage viscosity are compared. When using viscosity reducing excipients the processing time can be decreased from about 2 hours to about 1.4 hours. At the same time when using viscosity reducing excipients the system pressure remains lower than the system pressure for a comparable formulation lacking said excipients. It is clear that a further reduction of processing time is feasible if a higher system pressure is well tolerated by the protein and a higher flow rate can be used. Moreover, a 30% higher concentration was reached using viscosity reducing excipients.

FIGURE LEGENDS

Figure 1:
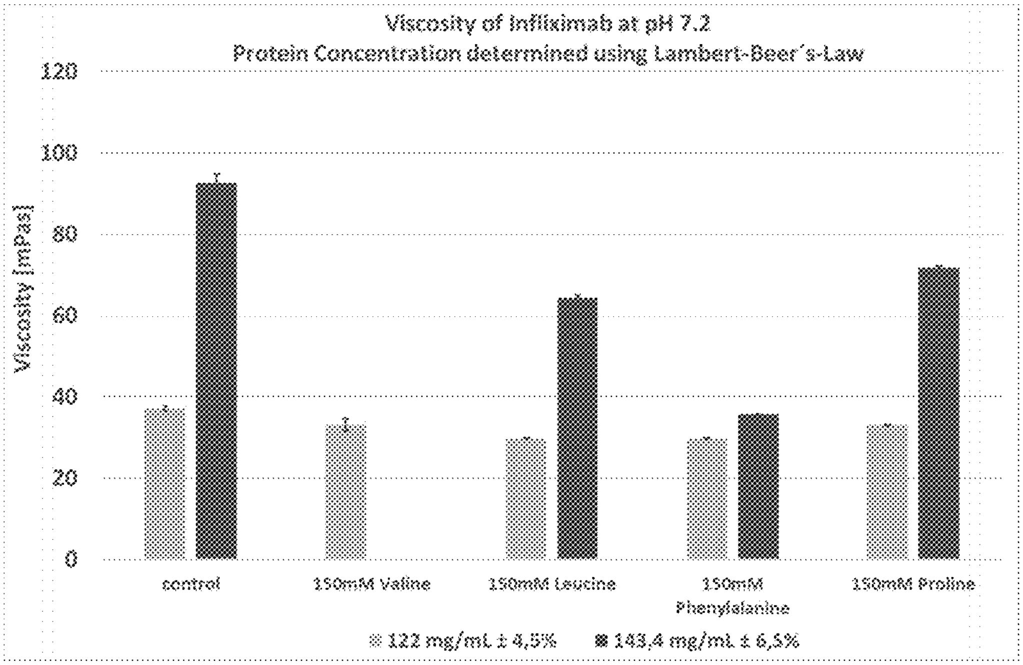
FIG. 1 shows the viscosity of Infliximab at pH 7.2, with the protein concentration determined using Lambert-Beer's law, using valine, leucine, phenylalanine and proline as excipients.
Figure 2:
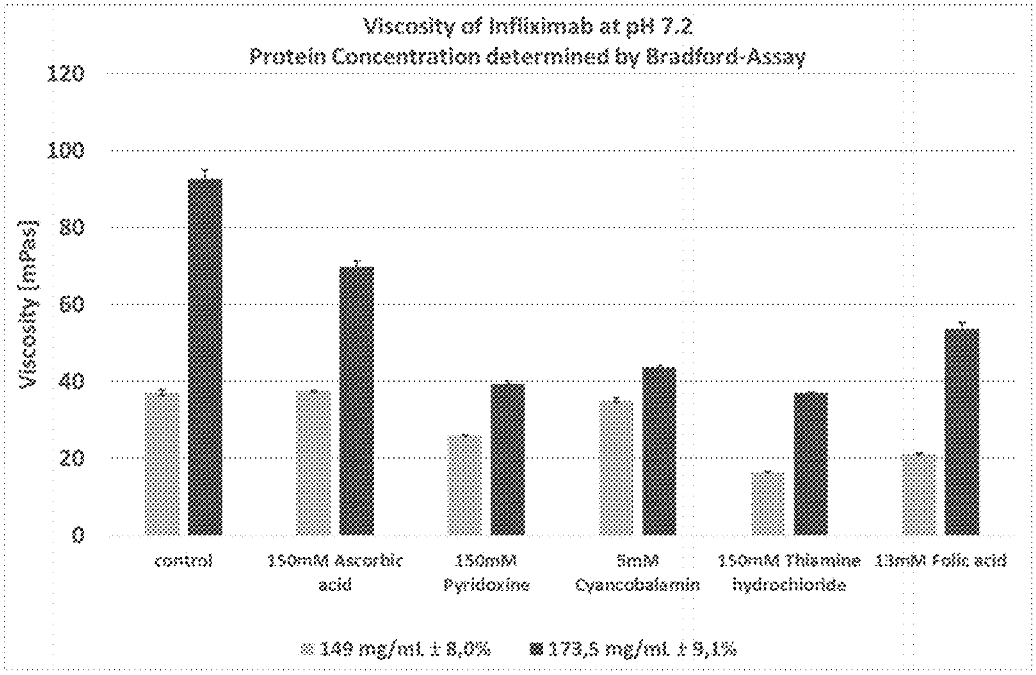
FIG. 2 shows the viscosity of Infliximab at pH 7.2, with the protein concentration determined using Bradford assay, using ascorbic acid, cyanocobalamin, thiamine hydrochloride, folic acid, thiamine pyrophosphate and thiamine monophosphate as excipients.
Figure 3:
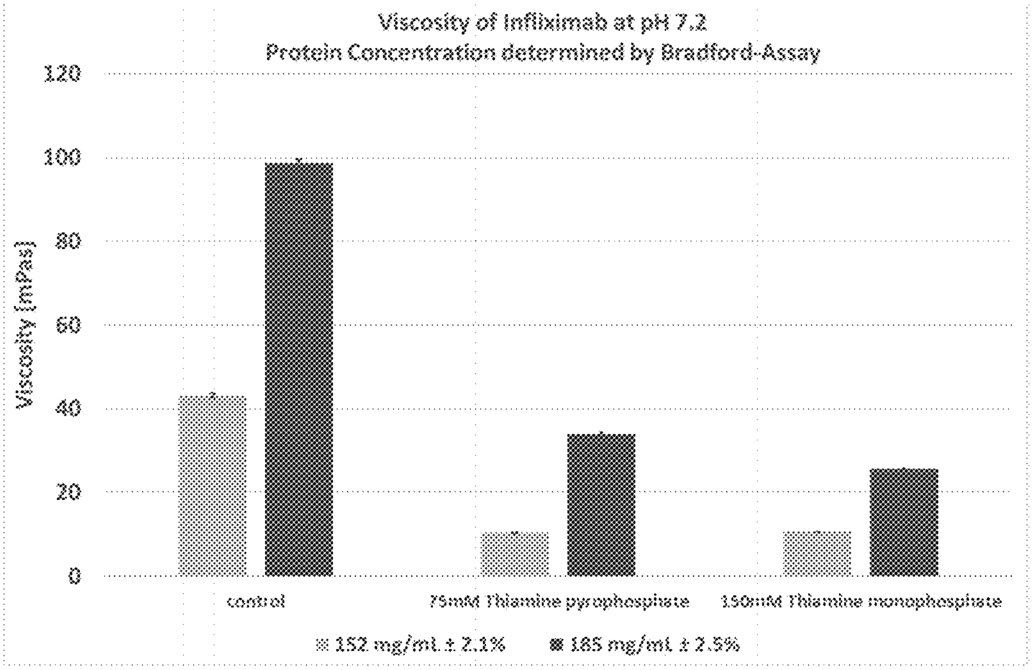
FIG. 3 shows the viscosity of Infliximab at pH 7.2, with the protein concentration determined using Bradford assay, using thiamine monophosphate and thiamine pyrophosphate as excipients.
Figure 4:
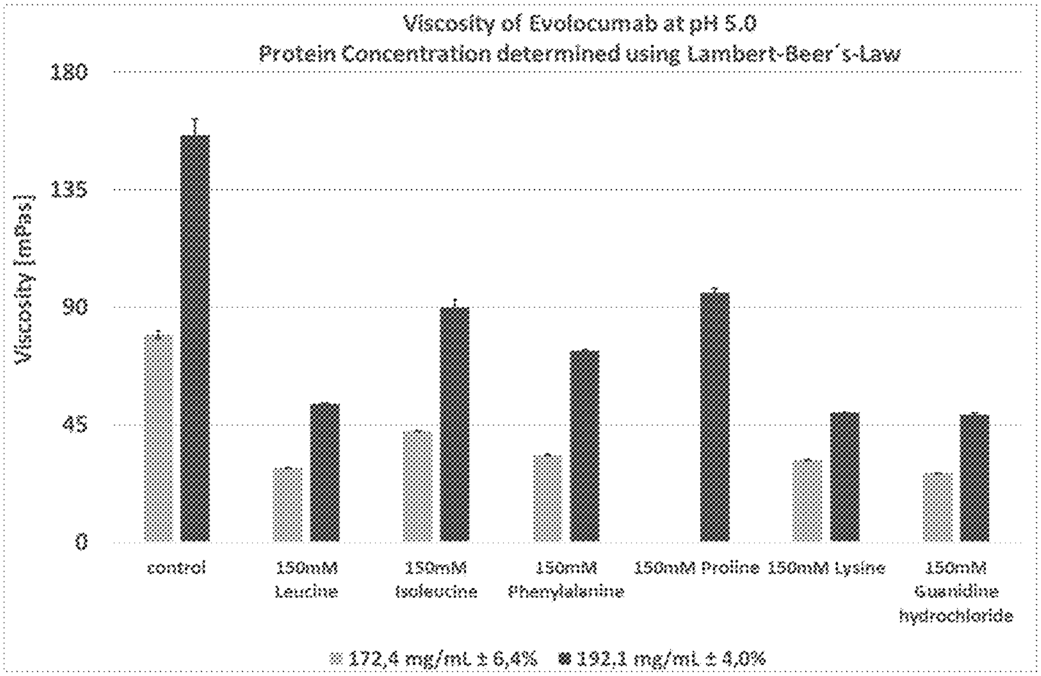
FIG. 4 shows the viscosity of a Evolocumab solution at pH 5.0, with the protein concentration determined using Lambert-Beer's law, using leucine, isoleucine, phenylalanine, proline, lysine and guanidine hydrochloride as excipients.
Figure 5:
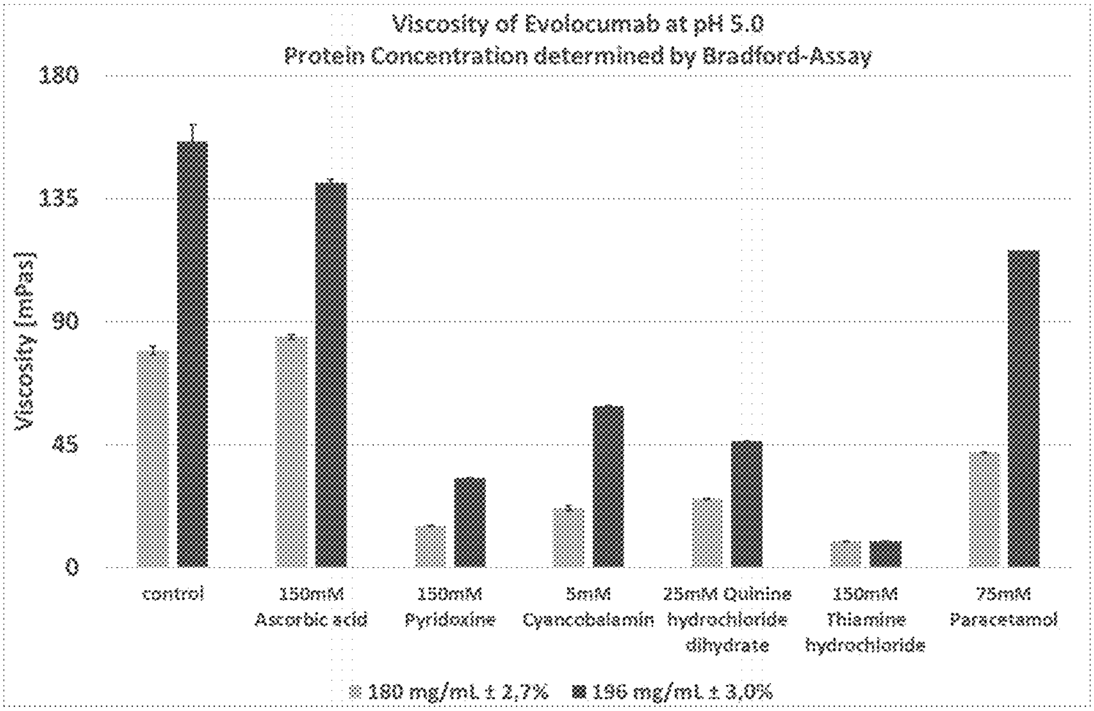
FIG. 5 shows the viscosity of a Evolocumab solution at pH 5.0, with the protein concentration determined using Bradford assay, using ascorbic acid, pyridoxine, cyanocobalamin, quinine hydrochloride dihydrate, thiamine hydrochloride and paracetamol as excipients.
Figure 6:
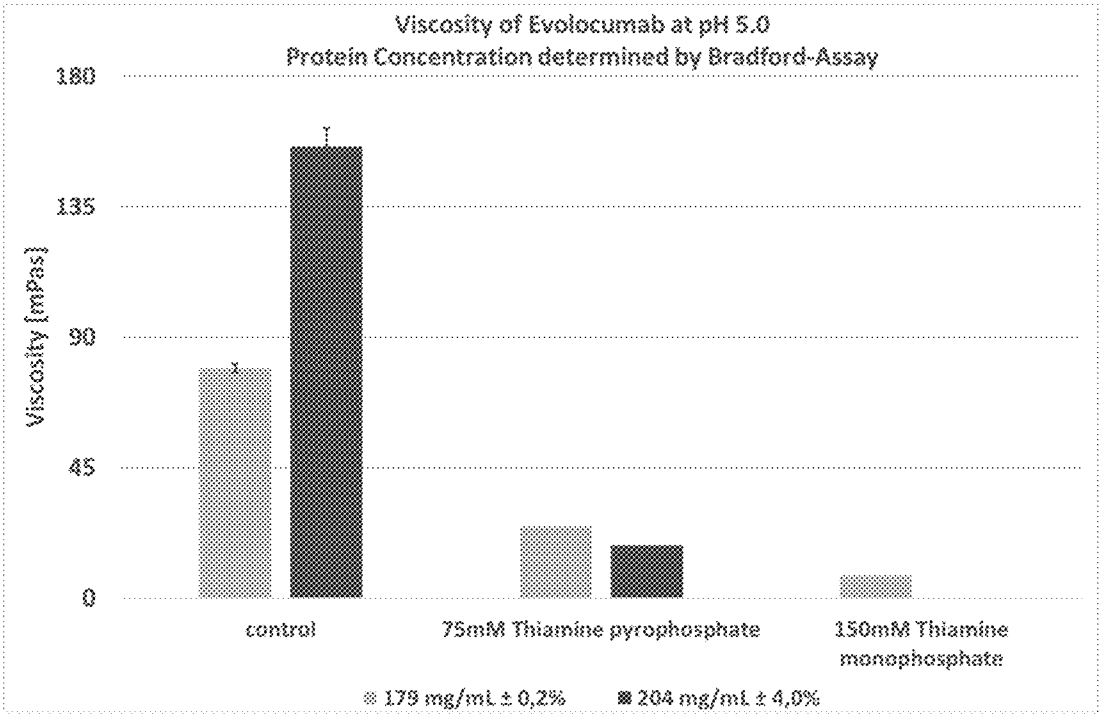
FIG. 6 shows the viscosity of a Evolocumab solution at pH 5.0, with the protein concentration determined using Bradford assay, using thiamine pyrophosphate and thiamine hydrochloride, thiamine monophosphate as excipients.
Figure 7:
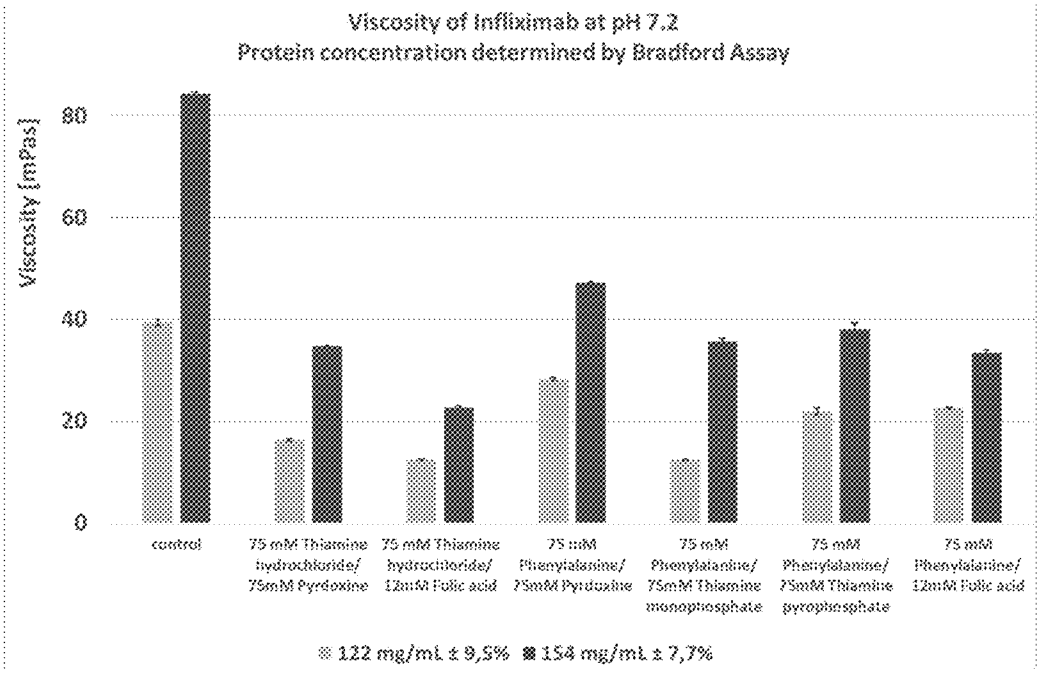
FIG. 7 shows the viscosity of a Infliximab solution at pH 7.2, with the protein concentration determined using Bradford assay, using combinations of thiamine hydrochloride, pyridoxine, folic acid, thiamine monophosphate and thiamine pyrophosphate as excipients.
Figure 8:
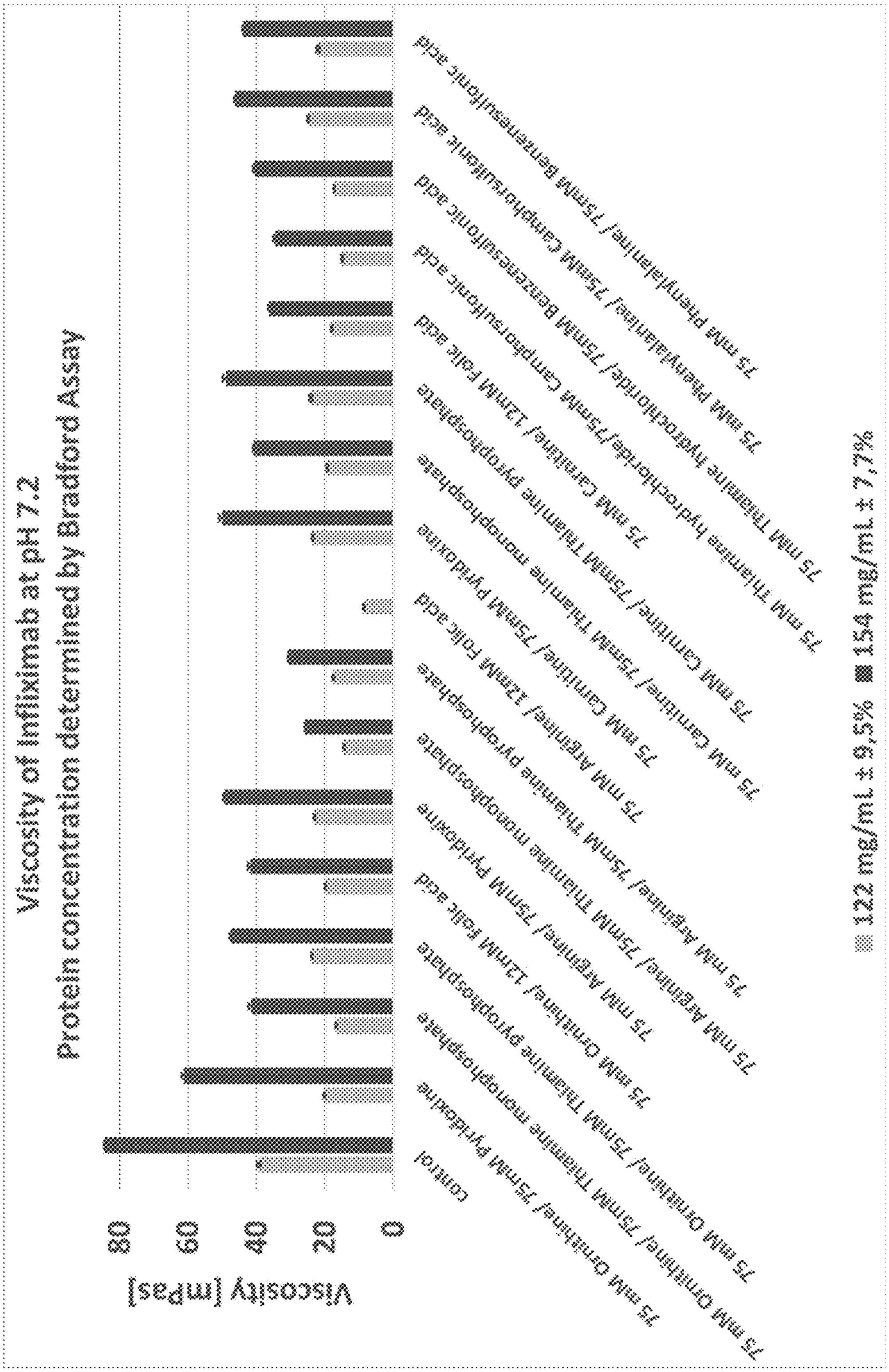

FIG. 8 shows the viscosity of a Infliximab solution at pH 7.2, with the protein concentration determined using Bradford assay, using combinations of a first set consisting of L-ornithine, L-arginine, L-carnitine, camphorsulfonic acid and benzenesulfonic acid and a second set consisting of thiamine hydrochloride, phenylalanine, pyridoxine, folic acid, thiamine monophosphate and thiamine pyrophosphate as excipients.

Figure 9:
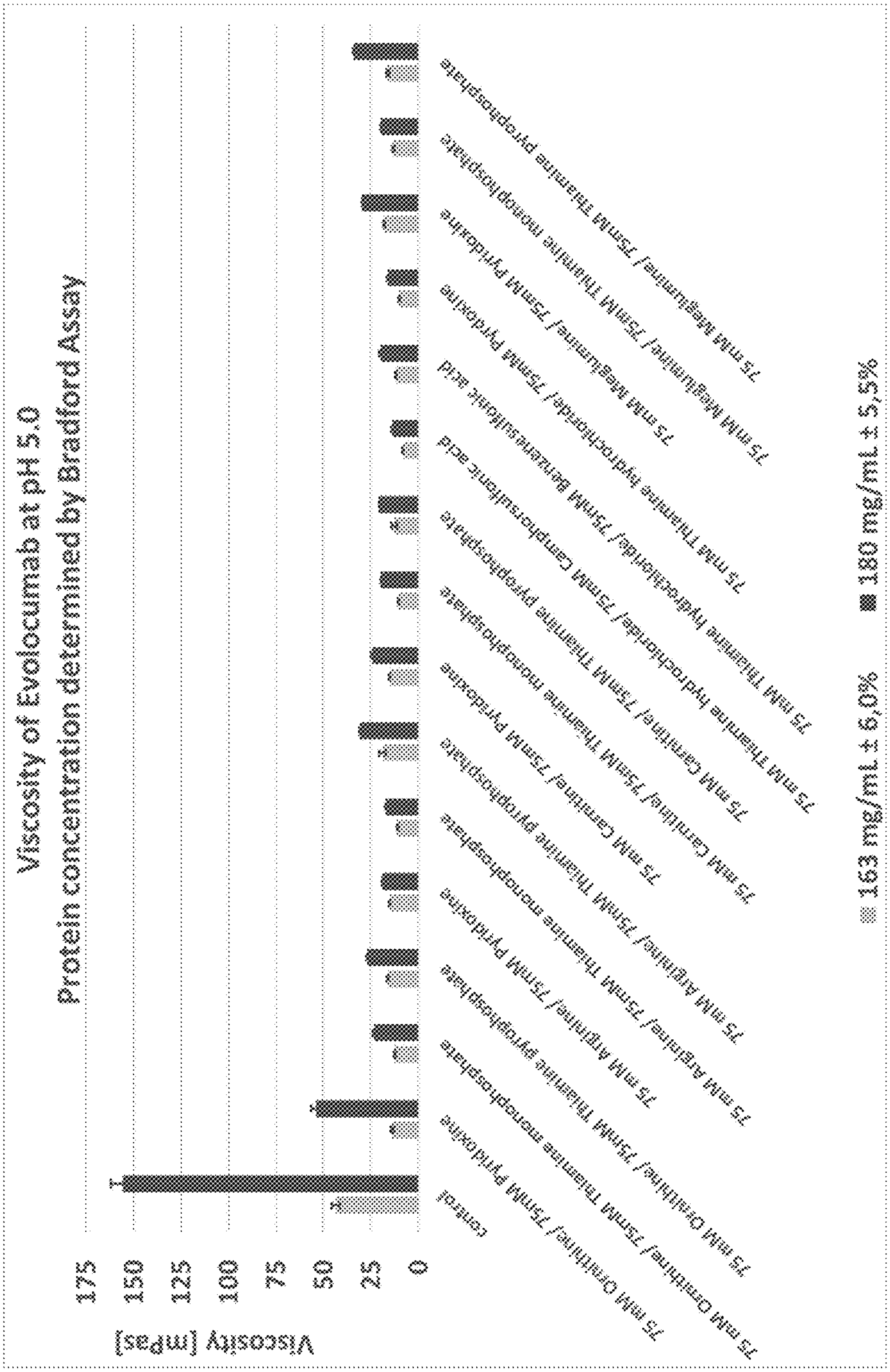

FIG. 9 shows the viscosity of a Evolocumab solution at pH 5.0, with the protein concentration determined using Bradford assay, using combinations of a first set consisting of L-ornithine, L-arginine, L-carnitine, meglumine, camphorsulfonic acid and benzenesulfonic acid and a second set consisting of thiamine hydrochloride, pyridoxine, thiamine monophosphate and thiamine pyrophosphate as excipients.

Figure 10:
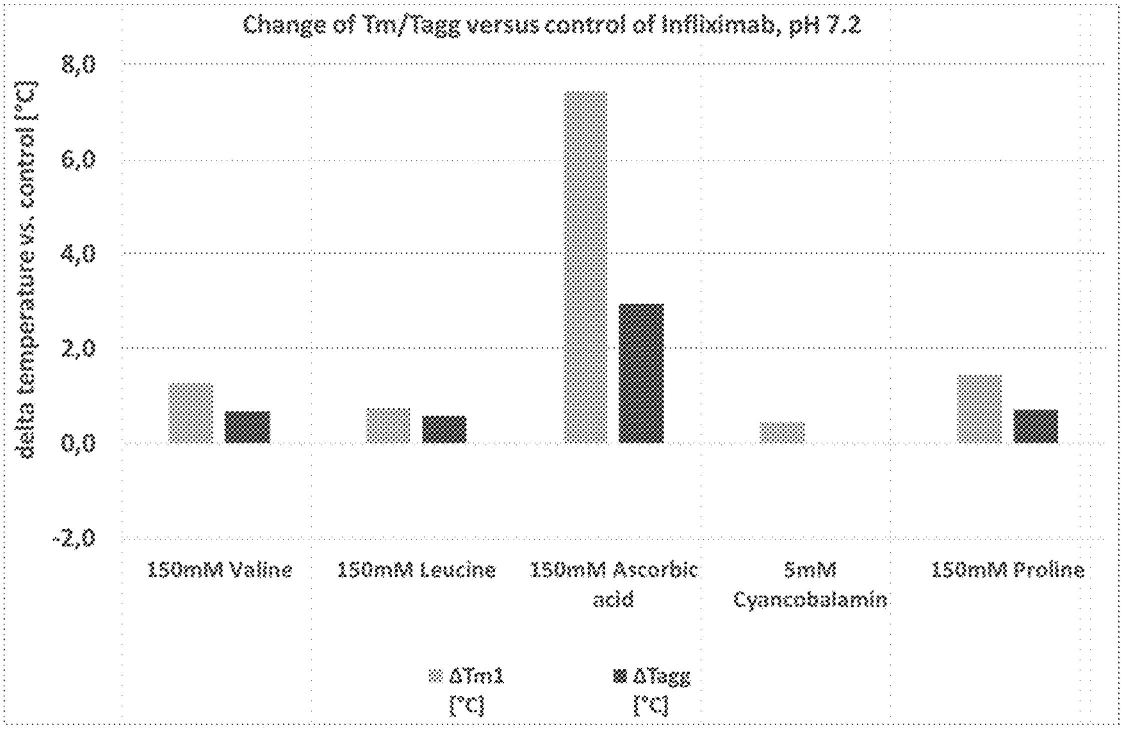

FIG. 10 shows the change of Tm/Tagg of compositions using valine, leucine, ascorbic acid, cyanocobalamin and proline as excipients, compared to a control of a Inliximab solution at pH 7.2.

Figure 11:
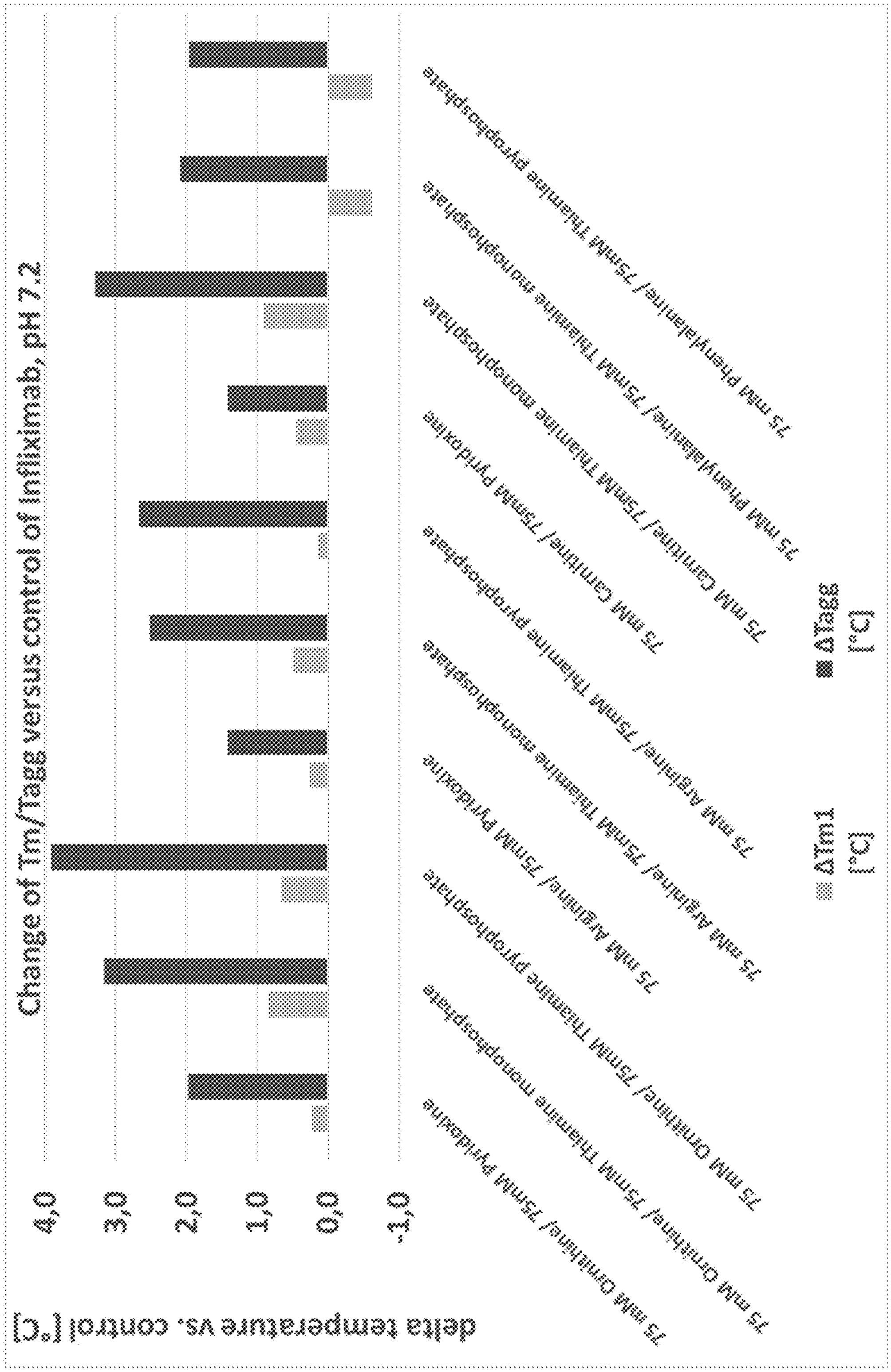

FIG. 11 shows the change of Tm/Tagg of compositions using combinations of a first set consisting of L-ornithine, L-arginine, L-carnitine, phenylalanine and benzenesulfonic acid and a second set consisting of pyridoxine, thiamine monophosphate and thiamine pyrophosphate compared to a control of a Infliximab solution at pH 7.2.

Figure 12:
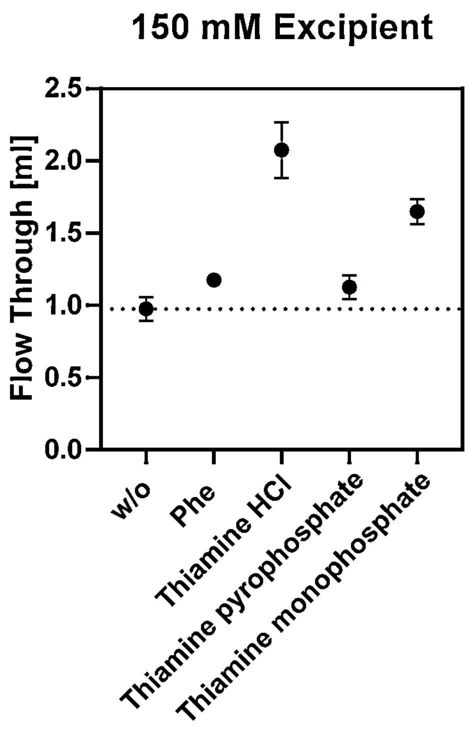
Figure 13:
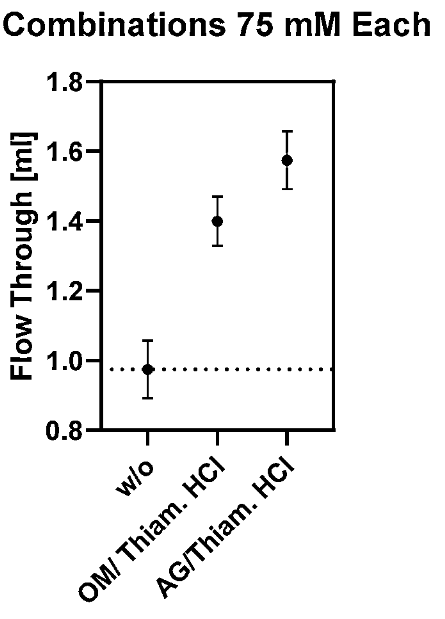

FIGS. 12 and 13, show the process improvement of viscosity reducing excipients and combinations thereof indicated by an increased permeate flux.

Figure 14:
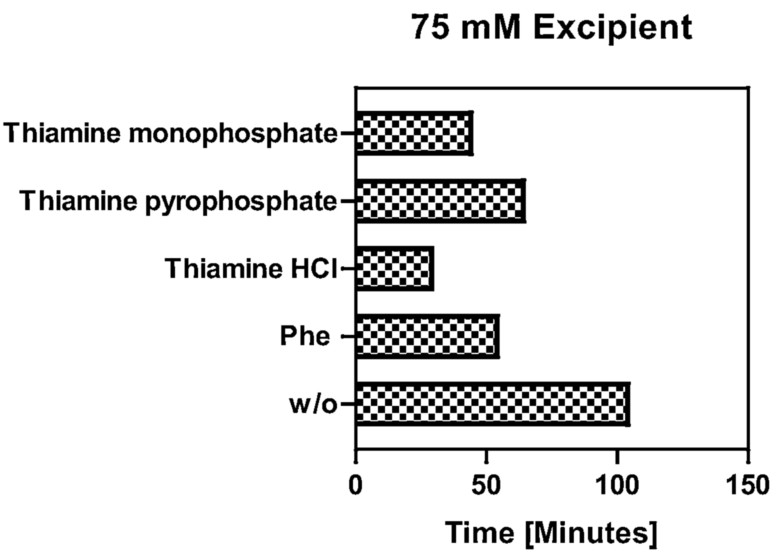
Figure 15:
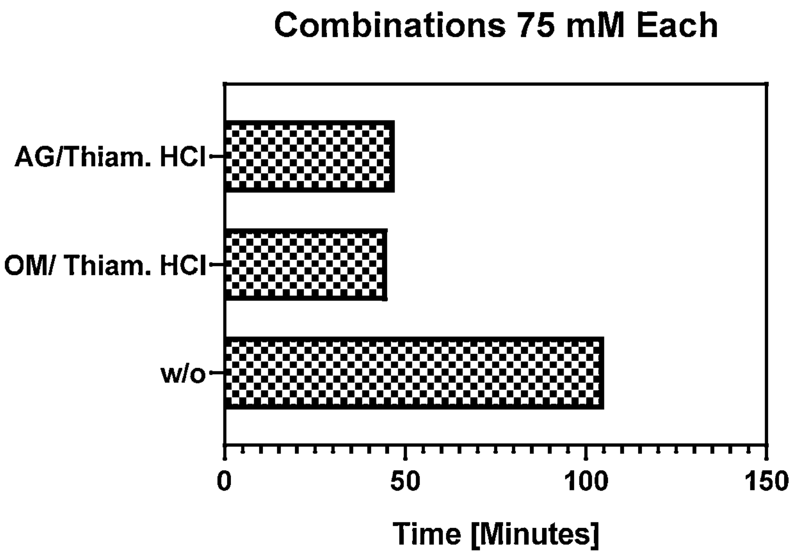

FIGS. 14 and 15 show the decrease in process time that can be achieved by the viscosity reducing excipients and combinations thereof.

Figure 16:
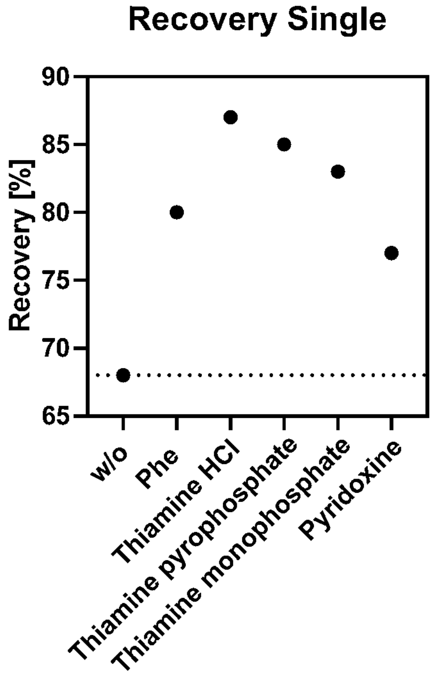

FIG. 16 shows the effect of viscosity reducing excipients on protein recovery.

Figure 17:
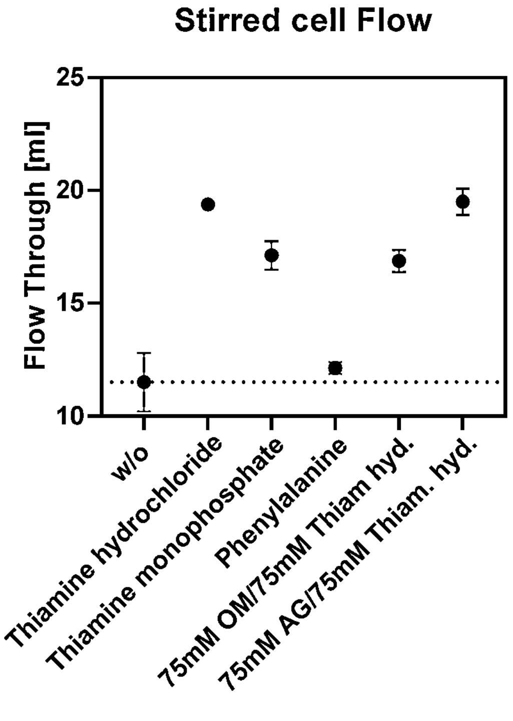

FIG. 17 shows the process improvement of viscosity reducing excipients and combinations thereof on indicated by an increased permeate flux in Amicon® stirred Cell filtration.

Figure 18:
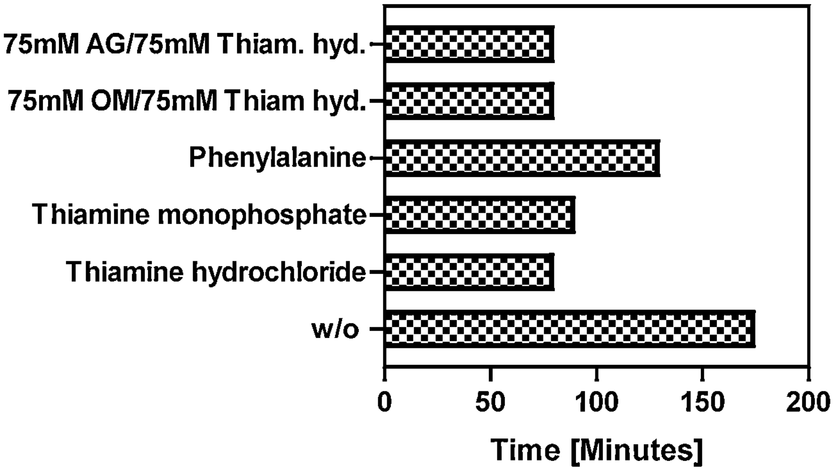

FIG. 18 shows the decrease in process time that can be achieved by the viscosity reducing excipients and combinations thereof in Amicon® stirred Cell filtration.

Figure 19:
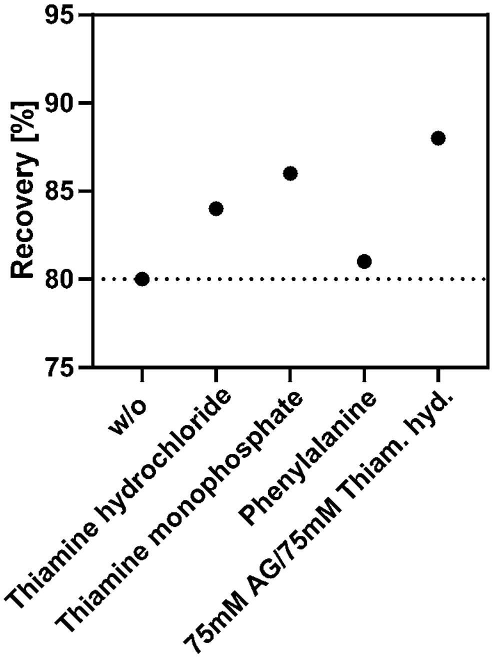

FIG. 19 shows the effect of viscosity reducing excipients and combinations thereof on protein recovery in Amicon® stirred Cell filtration.

Figure 20:
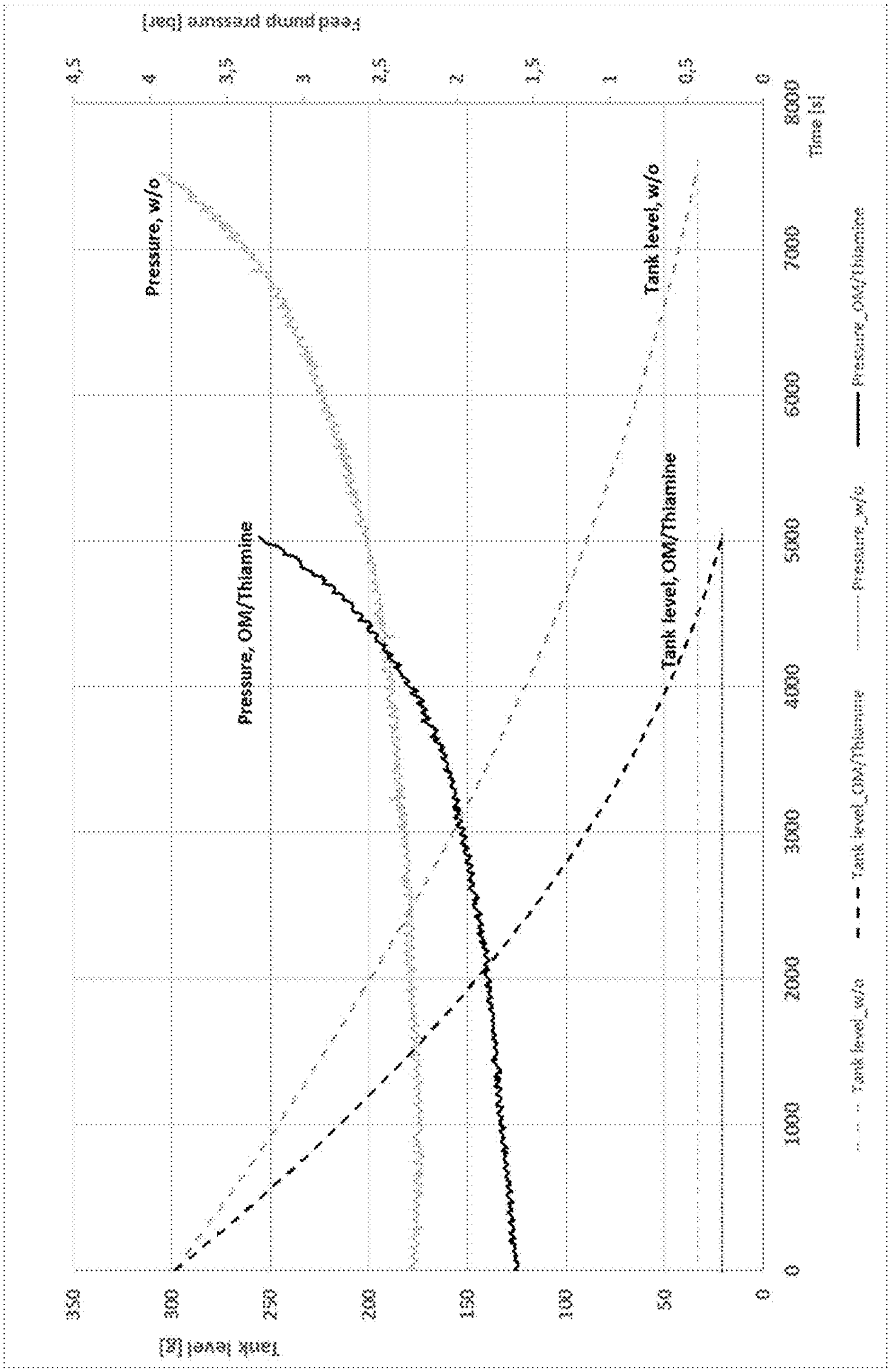

FIG. 20 shows the effect of viscosity reducing excipients and combinations thereof on the tank level with the pressure plotted vs. the process time in a tangential flow filtration system.

Figure 21:
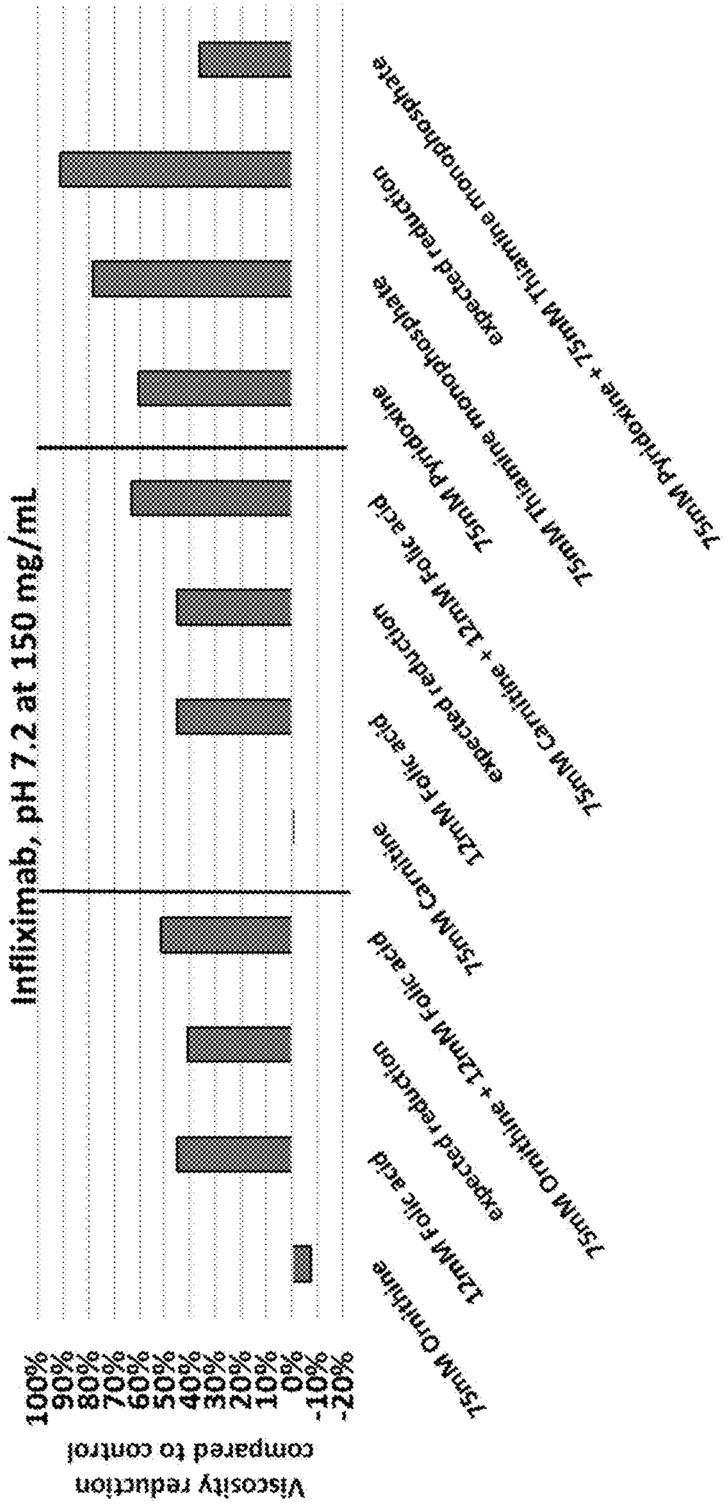

FIG. 21 shows the percentual viscosity reduction of an Infliximab formulation at 150 mg/mL, pH 7.2 upon addition of Ornthine, Folic acid and combination thereof, Carnitine, Folic acid and combination thereof as well as of Pyridoxine, Thiamine monophosphate and combination thereof. The expected reduction was calculated as described in 1.6.

Figure 22:
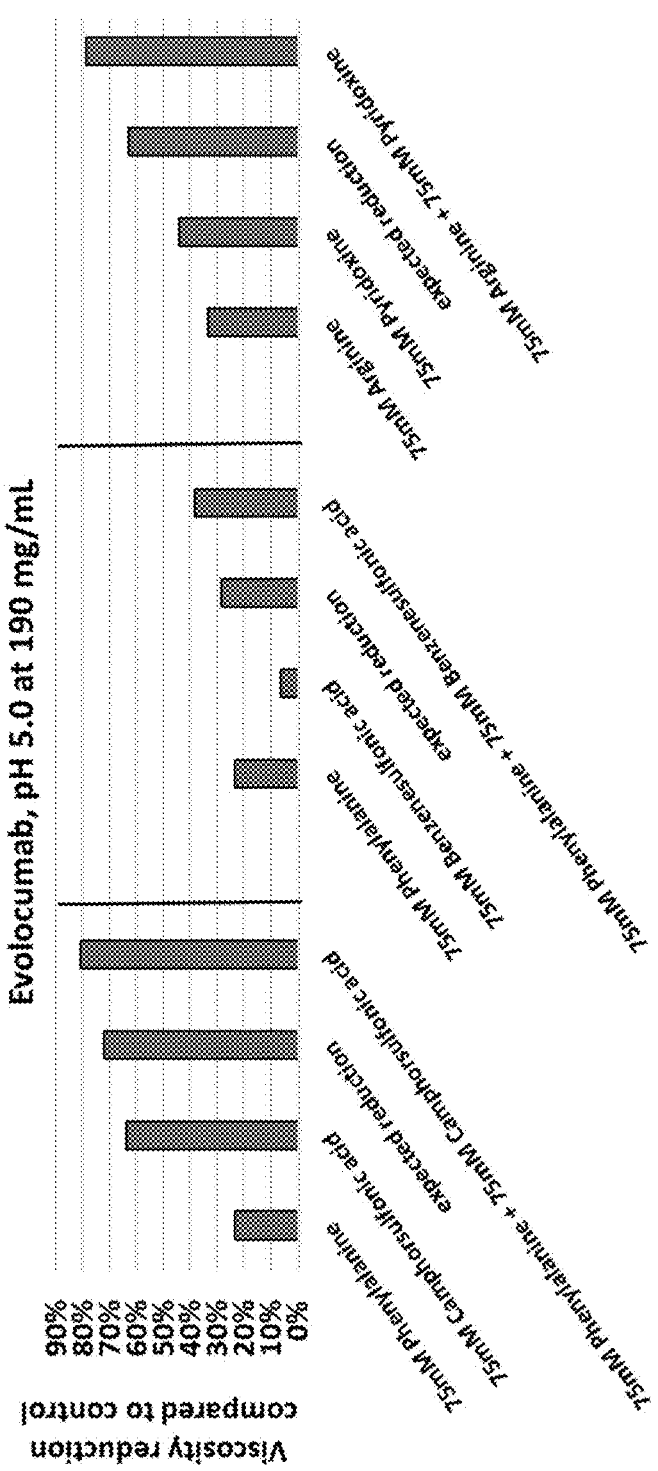

FIG. 22 shows the percentual viscosity reduction of an Evolocumab formulation at 190 mg/mL, pH 5.0 upon addition of Phenylalanine, Camphorsulfonic acid and combination thereof, Phenylalanine, Benzenesulfonic acid and combination thereof as well as of Arginine, Pyridoxine and combination thereof. The expected reduction was calculated as described in 1.6.

Figure 23:
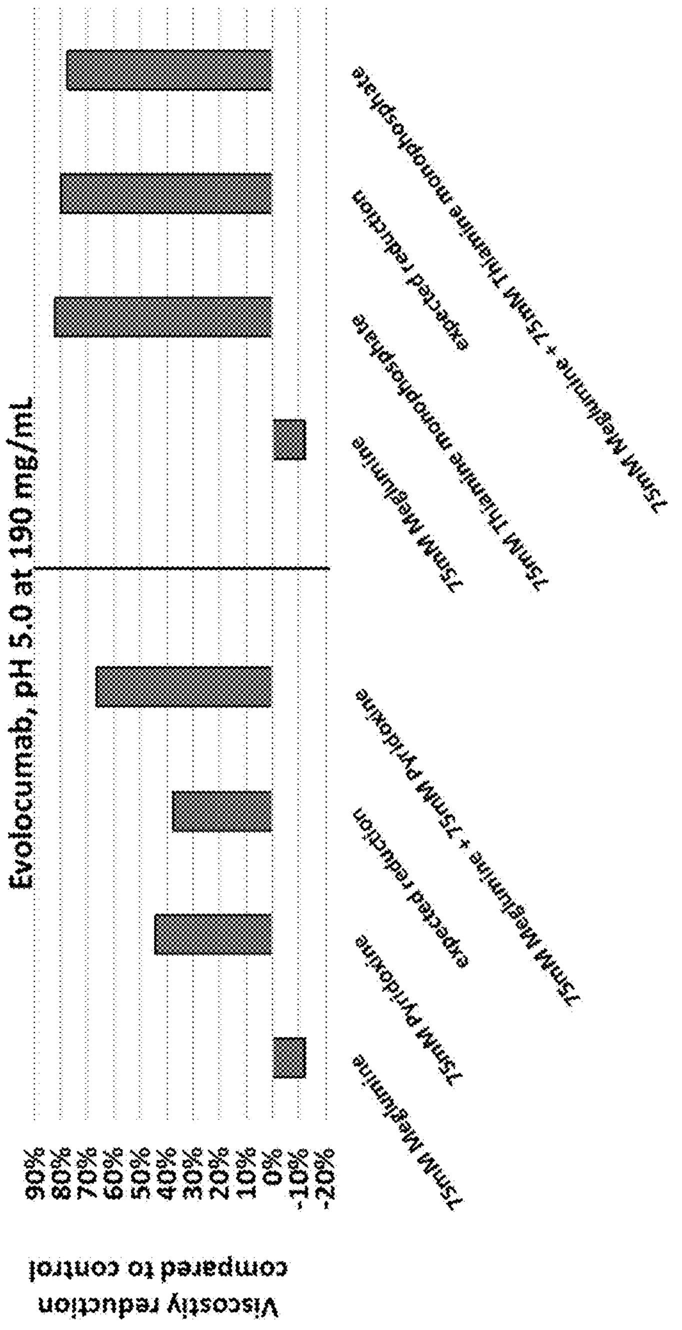

FIG. 23 shows the percentual viscosity reduction of an Evolocumab formulation at 190 mg/mL, pH 5.0 upon addition of Meglumine, Pyridoxine and combination thereof, Meglumine as well as of Meglumine, Thiamine monophosphate and combination thereof. The expected reduction was calculated as described in 1.6.

REFERENCES 901003.5.1-mVROC_User's_Manual

Guo Z. et al., "Structure-Activity Relationship for Hydrophobic Salts as Viscosity-Lowering Excipients for Concentrated Solutions of Monoclonal Antibodies", *Pharmaceutical Research;* 2012, 29(11):3102-9

Hung et al., "During production of concentrated monoclonal antibody formulations by tangential flow ultrafiltration (TFF), high viscosities and aggregation often cause extensive membrane fouling, flux decay and low product yields", *Journal of Membrane Science*, Volume 508, 15 Jun. 2016, Pages 113-126

The invention claimed is:

1. A liquid composition, comprising:

an antibody in a concentration of 90 mg/ml to 300 mg/ml, and one of the following viscosity reducing excipient combinations (i), (ii) or (iii):

(i) 5 mM to 300 mM of pyridoxine and 5 mM to 300 mM of meglumine, (ii) 5 mM to 300 mM of pyridoxine and 5 mM to 300 mM of ornithine, or (iii) 5 mM to 300 mM of pyridoxine and 5 mM to 300 mM of phenylalanine.

2. The liquid composition according to claim 1, having a reduced viscosity compared to an otherwise identical composition, but not comprising any one of the following viscosity reducing excipients (i), (ii) or (iii).

3. The liquid composition according to claim 1, wherein the liquid composition has a pH of 4 to 8.

4. The liquid composition according to claim 1, wherein the liquid composition further comprises a phosphate buffer or an acetate buffer at a concentration of 5 mM to 50 mM and a stabilizer.

5. The liquid composition according to claim 1, wherein the liquid composition has a viscosity of 1 mPas to 60 mPas at 20° C. as measured by a microfluidic viscometer.

6. The liquid composition according to claim 1, wherein the antibody is an IgG.

7. The liquid composition according to claim 1, comprising the viscosity reducing excipient combination (i).

8. The liquid composition according to claim 1, comprising the viscosity reducing excipient combination (ii).

9. The liquid composition according to claim 1, comprising the viscosity reducing excipient combination (iii).

10. A lyophilized antibody formulation of the liquid composition according to claim 1.

11. A method for reducing the viscosity of an antibody solution in a concentration of 90 mg/ml to 300 mg/ml, comprising adding to said protein solution one of the following viscosity reducing excipient combinations (i), (ii) or (iii):

(i) 5 mM to 300 mM of pyridoxine and 5 mM to 300 mM of meglumine, (ii) 5 mM to 300 mM of pyridoxine and 5 mM to 300 mM of ornithine, or (iii) 5 mM to 300 mM of pyridoxine and 5 mM to 300 mM of phenylalanine.

12. The method according to claim 11, wherein the antibody is an IgG.

13. The method according to claim 11, which is performed in a bioprocess.

14. The method according to claim 11, wherein the permeate flux of the protein solution in a filtration step is increased compared to an otherwise identical protein solution, but not comprising any one of the following viscosity reducing excipients (i), (ii) or (iii).

15. The method according to claim 11, comprising adding the viscosity reducing excipient combination (i).

16. The method according to claim 11, comprising adding the viscosity reducing excipient combination (ii).

17. The method according to claim 11, comprising adding the viscosity reducing excipient combination (iii).

* * * * *